US010302639B2

(12) United States Patent
Hirata et al.

(10) Patent No.: US 10,302,639 B2
(45) Date of Patent: May 28, 2019

(54) THERMAL TRANSFER MEDIUM FOR TESTING DEVICE, TESTING DEVICE AND METHOD FOR PRODUCING SAME, AND TESTING KIT

(71) Applicants: Miyuki Hirata, Mie (JP); Rie Kobayashi, Kanagawa (JP); Mio Akima, Tokyo (JP)

(72) Inventors: Miyuki Hirata, Mie (JP); Rie Kobayashi, Kanagawa (JP); Mio Akima, Tokyo (JP)

(73) Assignee: Ricoh Company, Ltd., Tokyo (JP)

( * ) Notice: Subject to any disclaimer, the term of this patent is extended or adjusted under 35 U.S.C. 154(b) by 160 days.

(21) Appl. No.: 15/382,148

(22) Filed: Dec. 16, 2016

(65) Prior Publication Data

US 2017/0176431 A1 Jun. 22, 2017

(30) Foreign Application Priority Data

Dec. 18, 2015 (JP) ................................ 2015-247422
Dec. 9, 2016 (JP) ................................ 2016-239845

(51) Int. Cl.

| | |
|---|---|
| ***G01N 21/75*** | (2006.01) |
| ***G01N 33/543*** | (2006.01) |
| ***G01N 33/558*** | (2006.01) |
| ***G01N 33/52*** | (2006.01) |

(52) U.S. Cl.
CPC ..... *G01N 33/54393* (2013.01); *G01N 33/525* (2013.01); *G01N 33/54386* (2013.01); *G01N 33/558* (2013.01)

(58) Field of Classification Search
CPC ....... G01N 33/54393; G01N 33/54386; G01N 33/525; G01N 33/558
See application file for complete search history.

(56) References Cited

U.S. PATENT DOCUMENTS

2010/0009456 A1* 1/2010 Prins .................... G01N 33/558 436/164
2012/0007971 A1 1/2012 Schnitzer et al.

FOREIGN PATENT DOCUMENTS

| | | | |
|---|---|---|---|
| EP | 3032260 A1 | 6/2016 | |
| JP | 3914442 | 2/2007 | |
| JP | 2015-034719 | 2/2015 | |
| JP | 2016-145789 | 8/2016 | |
| JP | 5989161 | 8/2016 | |
| WO | WO-2014133192 A1 * | 9/2014 | ............... B81C 1/00 |

OTHER PUBLICATIONS

Fridley et al,"Controlled release of dry reagents in porous media for tunable temporal and spatial distribution upon rehydration", Lab Chip. Nov. 7, 2012; 12(21): 4321-4327. (Year: 2012).*

* cited by examiner

*Primary Examiner* — Dennis White
(74) *Attorney, Agent, or Firm* — Oblon, McClelland, Maier & Neustadt, L.L.P.

(57) ABSTRACT

Provided is a thermal transfer medium for a testing device, the thermal transfer medium including a support, a solid-phase reagent layer provided over the support and containing a reagent over a surface of the solid-phase reagent layer; and a protective layer provided over the solid-phase reagent layer in a manner to cover the reagent, wherein an average thickness of the protective layer is 0.5 μm or greater but 30 μm or less.

10 Claims, 6 Drawing Sheets

THERMAL TRANSFER MEDIUM FOR TESTING DEVICE, TESTING DEVICE AND METHOD FOR PRODUCING SAME, AND TESTING KIT

CROSS-REFERENCE TO RELATED APPLICATIONS

The present application claims priority under 35 U.S.C. § 119 to Japanese Patent Application No. 2015-247422, filed Dec. 18, 2015 and Japanese Patent Application No. 2016-239845, filed Dec. 9, 2016. The contents of which are incorporated herein by reference in their entirety.

BACKGROUND OF THE INVENTION

Field of the Invention

The present invention relates to a thermal transfer medium for a testing device, a testing device and a method for producing the same, and a testing kit.

Description of the Related Art

Recently, in-vitro diagnostic devices intended for point of care testing (POCT) have been spreading rapidly. Representative examples used are testing devices employing a measuring method called "immunochromatography method" that can perform measurement without pretreatment and detects antigens in testing liquids utilizing specific reactivities possessed by antibodies.

Some of these testing devices are formed of, for example, sample pads as liquid receiving portions configured to receive testing liquids, conjugate pads in which the testing liquids supplied from the sample pads are allowed to undergo reactions, and membrane films in which the testing liquids supplied from the conjugate pads are allowed to flow.

For forming reagents such as labeled antibodies and antibodies as solid phases on, for example, fibers contained in flow path members of the testing devices, there are proposed, for example, a method of adding cyclic oligosaccharides to the reagents before forming the reagents as solid phases on the fibers in order to stably sustain the activities of the reagents (see, e.g., Japanese Unexamined Patent Application Publication No. 2015-34719), and a method of forming reagents such as antigens or antibodies as solid phases on, for example, fibers contained in flow path members and subsequently immersing the flow path members in buffer solutions in which sugars are dissolved to improve storage stability of the reagents (see, e.g., Japanese Patent No. 3914442).

SUMMARY OF THE INVENTION

According to one aspect of the present invention, a thermal transfer medium for a testing device is provided. The thermal transfer medium includes a support, a solid-phase reagent layer provided over the support and containing a reagent over a surface of the solid-phase reagent layer, and a protective layer provided over the solid-phase reagent layer in a manner to cover the reagent. An average thickness of the protective layer is 0.5 μm or greater but 30 μm or less.

Figure 1A:
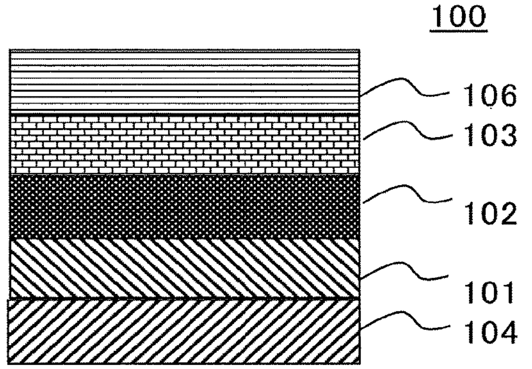
FIG. 1A is a schematic cross-sectional view of an example of a thermal transfer medium for a testing device according to an embodiment of the present invention.

DESCRIPTION OF THE EMBODIMENTS (Thermal Transfer Medium for Testing Device)

A thermal transfer medium for a testing device of the present invention includes a support, a solid-phase reagent layer provided over the support and containing a reagent over a surface of the solid-phase reagent layer, and a protective layer provided over the solid-phase reagent layer in a manner to cover the reagent. An average thickness of the protective layer is 0.5 μm or greater but 30 μm or less. The thermal transfer medium further includes other members as needed.

The thermal transfer medium for a testing device of the present invention is based on the following finding. In existing thermal transfer media for testing devices, a reagent immobilized to a solid-phase reagent layer is present in an exposed state and cannot be controlled in a stable structure. This makes the reagent likely to lose activity to be weaken in the ability to react with analytes, resulting in reduced measurement sensitivity.

The thermal transfer medium for a testing device of the present invention is also based on the following finding. Existing thermal transfer media for testing devices include a back layer over a surface of the support opposite to the surface over which the solid-phase reagent layer is provided. The existing thermal transfer media are produced in a sheet form and typically stored in a wound roll form. Therefore, the existing thermal transfer media have a poor temporal stability because the activity of the reagent (antibody)

degrades due to friction or impact between the back layer and the surface of the solid-phase reagent layer.

The present invention has an object to provide a thermal transfer medium for a testing device excellent in temporal stability of a solid-phase reagent and suitable for production of a testing device having an improved visibility.

The present invention can provide a thermal transfer medium for a testing device excellent in temporal stability of a solid-phase reagent and suitable for production of a testing device having an improved visibility.

The thermal transfer medium for a testing device of the present invention includes a support, a solid-phase reagent layer provided over the support and containing a reagent over a surface of the solid-phase reagent layer, and a protective layer provided over the solid-phase reagent layer in a manner to cover the reagent, and preferably includes a back layer over a surface of the support opposite to the surface over which the solid-phase reagent layer is provided.

The phrase "a protective layer being provided over the solid-phase reagent layer in a manner to cover the reagent" refers to a state that the protective layer covers at least a part of the reagent. Therefore, the protective layer may cover the whole of the reagent, or the protective layer may cover a part of the reagent so long as the effect of the present invention is obtained.

It is more preferable that the thermal transfer medium for a testing device include a release layer between the support and the solid-phase reagent layer, or that the solid-phase reagent layer be a release and solid-phase reagent layer serving also as a release layer. In a first mode, the thermal transfer medium for a testing device of the present invention includes a support, a release layer provided over the support, a solid-phase reagent layer provided over the release layer, and a protective layer provided over the solid-phase reagent layer, and further includes other members as needed.

A surface of the solid-phase reagent layer contains a reagent. The reagent is preferably an antibody. Examples of the antibody include a capture antibody.

In a second mode, the thermal transfer medium for a testing device of the present invention includes a support, a release and solid-phase reagent layer provided over the support, and a protective layer provided over the release and solid-phase reagent layer, and further includes other members as needed.

A surface of the release and solid-phase reagent layer contains a reagent. The reagent is preferably an antibody. Examples of the antibody include a capture antibody.

In both of the first mode and the second mode of the thermal transfer medium for a testing device, temporal stability of the reagent formed as a solid phase over the surface of the solid-phase reagent layer is improved by the protective layer. Although the reagent is covered by the protective layer, the reagent is not disturbed by the protective layer from reacting with the analyte, or rather may be promoted to react with the analyte. That is, when the protective layer is formed of a sugar, the protective layer improves hydrophilicity of the reagent because the sugar has hygroscopicity. This makes it easier for the reagent and a testing liquid to contact each other in a testing device to which the thermal transfer medium for a testing device is transferred, leading to an improved visibility.

Figure 1B:
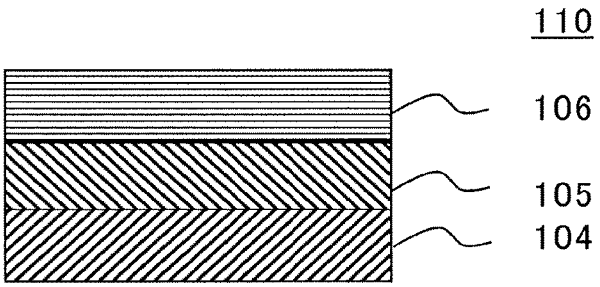
FIG. 1B is a schematic cross-sectional view of another example of a thermal transfer medium for a testing device according to an embodiment of the present invention.

The thermal transfer medium for a testing device of the present invention used for providing a resin layer over a flow path member will be described with reference to the drawings. FIG. 1A and FIG. 1B are schematic cross-sectional views of examples of thermal transfer media for a testing device according to embodiments of the present invention.

When employing a thermal transfer method, it is possible to use a thermal transfer medium 100 for a testing device to which a reagent (capture antibody) is previously attached uniformly. This can suppress variation in the concentration of the capture antibody along a test line or a control line. When coating and locating a capture antibody by an existing method, there is a need for diluting the capture antibody with a solvent until the capture antibody has a viscosity of a coatable level (e.g., a viscosity dischargeable by an inkjet printer). On the other hand, when locating a capture antibody by thermal transfer, use of a thermal transfer medium for a testing device to which a capture antibody is previously attached at a high concentration enables location of a capture antibody in a flow path at a high concentration.

As illustrated in FIG. 1A, the thermal transfer medium 100 for a testing device includes a support 101, a release layer 102 provided over the support 101, and a solid-phase reagent layer 103 provided over the release layer 102. A reagent (not illustrated) is formed as a solid phase over a surface of the solid-phase reagent layer 103. A protective layer 106 is provided over the solid-phase reagent layer 103 in a manner to protect the solid-phase reagent by covering. The thermal transfer medium 100 for a testing device further includes other layers such as a back layer 104 as needed.

As illustrated in FIG. 1B, a thermal transfer medium 110 for a testing device may include a release layer and a solid-phase reagent layer in the form of a double-functioning release and solid-phase reagent layer 105.

<Support>

The support 101 may be of any shape, any structure, any size, any material, etc. that are not particularly limited and may be appropriately selected depending on the intended purpose.

The structure of the support may be a single-layer structure or a laminated structure.

The size of the support may be appropriately selected depending on, for example, the size of the testing device.

The material of the support 101 is not particularly limited and may be appropriately selected depending on the intended purpose. Examples of the material of the support 101 include polyesters such as polyethylene terephthalate (PET) and polyethylene naphthalate (PEN), polycarbonates, polyimide resins (PI), polyamides, polyethylenes, polypropylenes, polyvinyl chlorides, polyvinylidene chlorides, polystyrenes, styrene-acrylonitrile copolymers, and cellulose acetates. One of these materials may be used alone or two or more of these materials may be used in combination. Among these materials, polyethylene terephthalate (PET) and polyethylene naphthalate (PEN) are particularly preferable.

It is preferable to apply a surface activation treatment to the surface of the support 101 in order to improve close adhesiveness with the layer to be provided over the support 101. Examples of the surface activation treatment include glow discharge treatment and corona discharge treatment.

The support 101 may be kept even after the solid-phase reagent layer 103 is transferred together with the protective layer 106 onto a flow path member 12, or the support 101, etc. may be peeled and removed by means of the release layer 102 after the solid-phase reagent layer 103 and the protective layer 106 are transferred. When the release and solid-phase reagent layer 105 is used, the release and solid-phase reagent layer 105 may be completely transferred together with the protective layer 106 onto the flow path member 12, or a portion of the release and solid-phase reagent layer 105 including the surface over which the antibody is formed as a solid phase may be transferred with part of the release and solid-phase reagent layer 105 left over the support 101 side.

The support 101 is not particularly limited and may be an appropriately synthesized product or a commercially available product.

The average thickness of the support 101 is not particularly limited, may be appropriately selected depending on the intended purpose, and is preferably 3 μm or greater but 50 μm or less.

<Release Layer>

The release layer 102 has a function of improving releasability between the support 101 and the solid-phase reagent layer 103 during transfer. The release layer 102 has a function of thermally melting and becoming a low-viscosity liquid when heated with a heating/pressurizing unit such as a thermal head, and making it easier for the solid-phase reagent layer 103 to be separated at about the interface between the heated portion and the non-heated portion.

The release layer 102 contains a wax and a binder resin and further contains other components as needed.

The wax is not particularly limited and may be appropriately selected depending on the intended purpose. Examples of the wax include: natural waxes such as beeswax, carnauba wax, cetaceum, Japan wax, candelilla wax, rice bran wax, and montan wax; synthetic waxes such as paraffin wax, microcrystalline wax, oxidized wax, ozokerite, ceresin, ester wax, polyethylene wax, and polyethylene oxide wax; higher fatty acids such as margaric acid, lauric acid, myristic acid, palmitic acid, stearic acid, furoic acid, and behenic acid; higher alcohols such as stearic alcohol and behenyl alcohol; esters such as fatty acid ester of sorbitan; and amides such as stearin amide and oleic amide. One of these waxes may be used alone or two or more of these waxes may be used in combination. Among these waxes, carnauba wax and polyethylene wax are preferable because these waxes are excellent in releasability.

The binder resin is not particularly limited and may be appropriately selected depending on the intended purpose. Examples of the binder resin include ethylene-vinyl acetate copolymers, partially saponified ethylene-vinyl acetate copolymers, ethylene-vinyl alcohol copolymers, ethylene-sodium methacrylate copolymers, polyamides, polyesters, polyurethanes, polyvinyl alcohols, methylcellulose, carboxymethylcellulose, starch, polyacrylic acid, isobutylene-maleic acid copolymers, styrene-maleic acid copolymers, polyacrylamides, polyvinylacetals, polyvinyl chlorides, polyvinylidene chlorides, isoprene rubbers, styrene-butadiene copolymers, ethylene-propylene copolymers, butyl rubbers, and acrylonitrile-butadiene copolymers. One of these binder resins may be used alone or two or more of these binder resins may be used in combination.

The method for forming the release layer 102 is not particularly limited and may be appropriately selected depending on the intended purpose. Examples of the method include a hot melt coating method, and a method of coating a coating liquid obtained by dispersing the wax and the binder resin in a solvent.

The average thickness of the release layer 102 is not particularly limited, may be appropriately selected depending on the intended purpose, and is preferably 0.5 μm or greater but 50 μm or less.

The amount of the release layer 102 to be attached is not particularly limited, may be appropriately selected depending on the intended purpose, and is preferably 0.5 $g/m^2$ or greater but 50 $g/m^2$ or less.

<Solid-Phase Reagent Layer>

The solid-phase reagent layer 103 needs to contain a resin to constitute a resin layer 15 of a testing device 10 described below. The material of the solid-phase reagent layer is not particularly limited and may be appropriately selected depending on the intended purpose.

The method for forming the solid-phase reagent layer 103 is not particularly limited and may be appropriately selected depending on the intended purpose. Examples of the method include a hot melt coating method and a method of coating a solid-phase reagent layer coating liquid obtained by dispersing the resin in a solvent on the support 101 or the release layer 102 by a common coating method such as a gravure coater, a wire bar coater, and a roll coater, and drying the coated liquid.

The average thickness of the solid-phase reagent layer 103 is not particularly limited, may be appropriately selected depending on the intended purpose, and is preferably 200 nm or greater but 50 μm or less. When the average thickness of the solid-phase reagent layer 103 is 200 nm or greater, the resin layer has an improved durability and can be prevented from being damaged by, for example, friction and impact. When the average thickness of the solid-phase reagent layer 103 is 50 μm or less, heat from a thermal head can be uniformly conducted to the solid-phase reagent layer 103, resulting in a good definition.

The amount of the solid-phase reagent layer 103 attached is not particularly limited, may be appropriately selected depending on the intended purpose, and is preferably 0.2 $g/m^2$ or greater but 50 $g/m^2$ or less. When the amount of the solid-phase reagent layer 103 attached is 0.2 $g/m^2$ or greater, the coating amount is appropriate and no deficiency is created in the resin layer. When the amount of the solid-phase reagent layer 103 attached is 50 $g/m^2$ or less, a drying time is appropriate and no unevenness is formed in the resin layer.

<Release and Solid-Phase Reagent Layer>

The release and solid-phase reagent layer 105 has functions of both of a release layer and a solid-phase reagent layer. The release and solid-phase reagent layer 105 can improve releasability between the support 101 and the solid-phase reagent layer 103 during transfer. Further, because the resin to constitute the resin layer 15 of the testing device 10 described below is contained in the release and solid-phase reagent layer 105, a reagent such as a capture antibody 17 or a capture antibody 18 can be formed as a solid phase over the release and solid-phase reagent layer 105.

When the release and solid-phase reagent layer 105 is heated with a heating/pressurizing unit such as a thermal head, a surface of the release and solid-phase reagent layer 105 contacting the support 101 thermally melts and becomes a low-viscosity liquid (heated portion), whereas a surface of the release and solid-phase reagent layer 105 over which the reagent is formed as a solid phase becomes a solid state or a state close to the solid state (non-heated portion). Therefore, the release and solid-phase reagent layer 105 has a function of facilitating separation at about the interface between the heated portion and the non-heated portion.

The release and solid-phase reagent layer 105 contains a wax and a binder resin, and further contains other components as needed.

The wax is not particularly limited and may be appropriately selected depending on the intended purpose. Examples of the wax include the same waxes as raised as examples for the release layer 102. One of these waxes may be used alone or two or more of these waxes may be used in combination.

Among these waxes, carnauba wax and polyethylene wax are preferable because these waxes are excellent in releasability and ability to immobilize (hydrophobize) a capture antibody.

The binder resin is not particularly limited and may be appropriately selected depending on the intended purpose. Examples of the binder resin include the same binder resins as raised as examples for the release layer 102. One of these binder resins may be used alone or two or more of these binder resins may be used in combination.

The method for forming the release and solid-phase reagent layer 105 is not particularly limited and may be appropriately selected depending on the intended purpose. Examples of the method include a hot melt coating method, and a method of coating a coating liquid obtained by dispersing the wax and the binder resin in a solvent.

The average thickness of the release and solid-phase reagent layer 105 is not particularly limited, may be appropriately selected depending on the intended purpose, and is preferably 0.5 μm or greater but 50 μm or less. When the average thickness of the release and solid-phase reagent layer 105 is 0.5 μm or greater, the release and solid-phase reagent layer 105 has an improved durability and can prevent a resin layer of a testing device from being damaged by, for example, friction and impact. When the average thickness of the release and solid-phase reagent layer 105 is 50 μm or less, heat from a thermal head can be uniformly conducted to the release and solid-phase reagent layer 105, resulting in a good definition.

The amount of the release and solid-phase reagent layer 105 attached is not particularly limited, may be appropriately selected depending on the intended purpose, and is preferably 0.5 $g/m^2$ or greater but 50 $g/m^2$ or less. When the amount of the release and solid-phase reagent layer 105 attached is 0.5 $g/m^2$ or greater, the coating amount is appropriate and no deficiency is created in the release and solid-phase reagent layer 105. When the amount of the release and solid-phase reagent layer 105 attached is 50 $g/m^2$ or less, a drying time is appropriate and no unevenness is formed in the release and solid-phase reagent layer 105.

—Formation of Solid-Phase Reagent—

After the coating liquid is dried and the solid-phase reagent layer 103 or the release and solid-phase reagent layer 105 is formed, a solution containing a labeled antibody 16 or a capture antibody (17 or 18) is coated over the surface of the solid-phase reagent layer 103 or the release and solid-phase reagent layer 105, to form a coating film. Subsequently, the coating film is dried. This makes it possible for the labeled antibody 16 or the capture antibody (17 or 18) to be formed as a solid phase over the surface of the solid-phase reagent layer 103 or the release and solid-phase reagent layer 105.

—Formation of Solid-Phase Labeled Antibody—

The method for forming the labeled antibody as a solid phase is not particularly limited and may be appropriately selected depending on the intended purpose. Examples of the method include a method of coating a coating liquid of the labeled antibody over the surface of the solid-phase reagent layer 103 or the release and solid-phase reagent layer 105 to form a water film and drying up the water film by, for example, natural drying, drying under reduced pressure, or freeze drying to form the water film as a solid phase.

It is preferable that the water film be coated to have a uniform thickness.

An amount of the labeled antibody coated is not particularly limited and may be appropriately selected depending on the intended purpose. When using a gold colloid labeled antibody as the labeled antibody, it is preferable to coat a gold colloid labeled antibody having an OD (optical density) of from 1.0 through 20 in a coating amount of 20 μL or greater but 600 μL or less per unit area ($cm^2$) of the resin layer. When the coating amount of the labeled antibody is 20 μL or greater, the amount of the gold colloid labeled antibody is appropriate and a color developing intensity on a line is good. When the coating amount of the labeled antibody is 600 μL or less, the amount of the gold colloid labeled antibody is appropriate and color development on a line is good.

The drying method is not particularly limited and may be appropriately selected depending on the intended purpose. Examples of the drying method include through-flow drying, vacuum drying, natural drying, and freeze drying. Among these drying methods, natural drying under a low humidity or drying under reduced pressure is preferable.

A humidity during drying is preferably 30% or lower on a relative humidity basis. When the relative humidity is 30% or lower, drying is appropriate and an antibody can be formed as a sufficiently solid phase.

A drying temperature for drying the coating liquid is not particularly limited, may be appropriately selected depending on the intended purpose, and is preferably −40 degrees C. or higher but 50 degrees C. or lower. When the drying temperature is −40 degrees C. or higher, drying of the coating liquid can be performed appropriately and productivity is improved. When the drying temperature is 50 degrees C. or lower, there is an advantage that the reagent can be prevented from being denatured by heat. However, it may be preferable to set the upper limit temperature to a temperature lower than 50 degrees C., depending on the kind of the labeled antibody.

A drying time for drying the coating liquid is not particularly limited, may be appropriately selected depending on the intended purpose, and is preferably 24 hours or shorter. When the drying time is 24 hours or shorter, there are advantages that productivity is improved and that discoloring can be prevented.

—Formation of Solid-Phase Capture Antibody—

The method for forming the capture antibody as a solid phase is not particularly limited and may be appropriately selected depending on the intended purpose. Examples of the method include a method (dry-up method) of coating a coating liquid of the capture antibody over the surface of the solid-phase reagent layer 103 or the release and solid-phase reagent layer 105 to form a water film and drying up the water film by, for example, natural drying, drying under reduced pressure, or freeze drying to form the water film as a solid phase, and a method (adsorption drying method) of leaving the coating liquid standing still under a high humidity environment so as not for the coating liquid to dry, cleaning the surface of the solid-phase reagent layer 103 or the release and solid-phase reagent layer 105 with, for example, distilled water as needed, and drying the coating liquid to a solid phase. In either case, it is preferable that the coating film be coated to have a uniform thickness.

The concentration of a buffer used for diluting the capture antibody is not particularly limited, and a buffer having a composition commonly used for diluting antibodies may be used. However, the concentration of the buffer is preferably 10 μg/mL or greater but 5,000 μg/mL or less and more preferably 100 μg/mL or greater but 1,000 μg/mL or less. When the coating concentration is 10 μg/mL or greater, the amount of the liquid coated per unit area ($cm^2$) of the solid-phase reagent layer 103 or the release and solid-phase reagent layer 105 is appropriate. This suppresses the amount coated of components such as an inorganic salt contained in the buffer, and makes it possible to form the antibody as a sufficiently solid phase. When the coating concentration is 5,000 μg/mL or less, wettability and viscosity of the coating liquid are appropriate. This makes coating over the solid-phase reagent layer 103 or the release and solid-phase reagent layer 105 good, with an appropriate amount of the liquid coated, resulting in formation of a uniform water film.

The drying method used when forming the capture antibody as a solid phase by the dry-up method is not particularly limited and may be appropriately selected depending on the intended purpose. Examples of the drying method include through-flow drying, vacuum drying, natural drying, and freeze drying. Among these drying methods, natural drying under a low humidity or drying under reduced pressure is preferable.

The humidity during drying is preferably 30% or lower on a relative humidity basis. When the relative humidity is higher than 30%, there is a risk that drying is insufficient and the antibody may not be able to be formed as a sufficiently solid phase.

The drying temperature for drying the coating liquid is not particularly limited, may be appropriately selected depending on the intended purpose, and is preferably −40 degrees C. or higher but 50 degrees C. or lower. When the drying temperature is −40 degrees C. or higher, drying of the coating liquid can be performed appropriately and productivity is improved. When the drying temperature is 50 degrees C. or lower, there is an advantage that the reagent can be prevented from being denatured by heat. However, it may be preferable to set the upper limit temperature to a temperature lower than 50 degrees C., depending on the kind of the capture antibody.

The drying time for drying the coating liquid is not particularly limited, may be appropriately selected depending on the intended purpose, and is preferably 24 hours or shorter. When the drying time is 24 hours or shorter, there are advantages that productivity is improved and that discoloring can be prevented.

Preferable conditions for standing still when forming the capture antibody as a solid phase by the adsorption drying method include a temperature of 0 degree C. or higher but 40 degrees C. or lower and a relative humidity of 30% or higher. When the temperature is 0 degree C. or higher, the capture antibody can be appropriately formed as a solid phase. When the temperature is 40 degrees C. or lower, the capture antibody is not denatured. When the relative humidity is 30% or higher, water volatilization during standing still is low, and this prevents any undesirable component other than the antibody from being formed as a solid phase in a large amount.

The cleaning method after standing still is not particularly limited and may be appropriately selected depending on the intended purpose. Examples of the cleaning method include a method of pouring, for example, distilled water in an amount of 20 μL or greater but 100 μL or less per unit area ($cm^2$) onto the surface for the solid phase formation using, for example, a shaker, and cleaning the surface at room temperature (20 degrees C.) by gentle shaking.

The drying method is not particularly limited and may be appropriately selected depending on the intended purpose. Examples of the drying method include through-flow drying, vacuum drying, natural drying, and freeze drying. Among these drying methods, natural drying under a low humidity or drying under reduced pressure is preferable.

The humidity during drying is preferably 30% or lower on a relative humidity basis. When the relative humidity is 30% or lower, drying is appropriate and the antibody can be formed as a sufficiently solid phase.

The drying temperature is not particularly limited, may be appropriately selected depending on the intended purpose, and is preferably higher than or equal to room temperature (20 degrees C.) but lower than or equal to 50 degrees C. However, it may be preferable to set the upper limit temperature to a temperature lower than 50 degrees C., depending on the kind of the capture antibody.

When the drying temperature is 20 degrees C. or higher, a drying time is appropriate and productivity is improved. When the drying temperature is 50 degrees C. or lower, the reagent can be prevented from being denatured by heat.

The drying time is not particularly limited, may be appropriately selected depending on the intended purpose, and is preferably 24 hours or shorter. When the drying time is 24 hours or shorter, productivity is improved and discoloring of the resin can be prevented.

The amount of the capture antibody formed as a solid phase is preferably 500 $ng/cm^2$ or greater. When the amount of the capture antibody formed as a solid phase is 500 $ng/cm^2$ or greater, the amount of the capture antibody formed as a solid phase is appropriate and a sufficient color developing intensity can be obtained on a line.

Examples of the method for analyzing the amount of the antibody formed as a solid phase over the surface of the resin layer include X-ray photoelectron spectroscopy (XPS).

<Protective Layer>

The protective layer 106 is not particularly limited and may be appropriately selected depending on the intended purpose, so long as the protective layer 106 protects the reagents immobilized to the surface of the solid-phase reagent layer 103 and the surface of the release and solid-phase reagent layer 105.

Protection by the protective layer 106 refers to protection for suppressing deactivation of the activities possessed by the reagents, and protection for preventing the structures of the reagents from being destroyed due to friction or impact when the reagents are overlapped with and rubbed against the back layer in a typical thermal transfer medium for a testing device formed into a sheet form and wound up.

The protective layer 106 contains a sugar and further contains other components as needed.

The sugar is not particularly limited and may be appropriately selected depending on the intended purpose. However, a monosaccharide and an oligosaccharide are preferable. Examples of the sugar include glucose, fructose, galactose, inositol, sucrose, lactose, maltose, trehalose, and cellobiose. One of these sugars may be used alone or two or more of these sugars may be used in combination.

Among these sugars, trehalose and inositol are preferable because these sugars contain many hydroxyl groups and become a strongly vitrified state. The vitrified state refers to a state that molecular motion in a component is so severely suppressed that the molecules neither crystallize nor melt but stay in an extremely stable solid state.

The content of the sugar in the protective layer is preferably 0.05% by mass or greater but 10% by mass or less.

The other components are not particularly limited and may be appropriately selected depending on the intended purpose.

The method for forming the protective layer 106 is not particularly limited and may be appropriately selected depending on the intended purpose. Examples of the method include a method of forming the capture antibody as a solid phase over the support and then coating and drying a protective layer coating liquid or a gel containing the sugar and a solvent. Examples of the solvent include water, ethanol, and a mixture solvent of water and ethanol.

The average thickness of the protective layer 106 is 5 μm or greater but 30 μm or less and more preferably 10 μm or greater but 20 μm or less.

When the average thickness of the protective layer is 5 μm or greater but 30 μm or less, the protecting function of the protective layer is sufficient, a reaction between the capture antibody and an analyte is facilitated, and a line having an excellent visibility can be obtained when the protective layer 106 is used in a testing device.

The average thickness of the protective layer can be calculated based on, for example, an amount of the protective layer added per area and the concentration of the protective layer coating liquid.

<Back Layer>

It is preferable that the thermal transfer medium 100 for a testing device include a back layer 104 over a surface of the support 101 opposite to the surface over which the release layer 102 is provided. During transfer, heat from, for example, a thermal head is directly applied to the opposite surface in a manner to match the shape of the resin layer. Therefore, it is preferable that the back layer 104 have resistance to a high heat and resistance to friction with, for example, the thermal head.

The back layer 104 contains a binder resin and further contains other components as needed.

The binder resin is not particularly limited and may be appropriately selected depending on the intended purpose. Examples of the binder resin include silicone-modified urethane resins, silicone-modified acrylic resins, silicone resins, silicone rubbers, fluororesins, polyimide resins, epoxy resins, phenol resins, melamine resins, and nitrocellulose. One of these binder resins may be used alone or two or more of these binder resins may be used in combination.

The other components are not particularly limited and may be appropriately selected depending on the intended purpose. Examples of the other components include inorganic particles of, for example, talc, silica, or organopolysiloxane, and a lubricant.

The method for forming the back layer 104 is not particularly limited and may be appropriately selected depending on the intended purpose. Examples of the method include a gravure coater, a wire bar coater, and a roll coater.

The average thickness of the back layer 104 is not particularly limited, may be appropriately selected depending on the intended purpose, and is preferably 0.01 μm or greater but 1.0 μm or less.

<Other Layers>

As the other layers, an undercoat layer may be provided between the support 101 and the release layer 102 and between the release layer 102 and the solid-phase reagent layer 103, or between the support 101 and the release and solid-phase reagent layer 105.

The undercoat layer contains a resin, and further contains other components as needed.

The resin is not particularly limited and may be appropriately selected depending on the intended purpose. Examples of the resin include the resins used in the solid-phase reagent layer 103, the release layer 102, and the release and solid-phase reagent layer 105.

(Method for Producing Testing Device)

The method for producing a testing device of the present invention includes a step of bringing the solid-phase reagent layer (or the release and solid-phase reagent layer) of the thermal transfer medium for a testing device of the present invention into contact with a porous flow path member to transfer the solid-phase reagent layer (or the release and solid-phase reagent layer) onto the flow path member (this step may hereinafter be referred to as "solid-phase reagent layer transfer step"), and further includes other steps as needed.

<Solid-Phase Reagent Layer Transfer Step>

Examples of the method for thermally transferring the solid-phase reagent layer (or the release and solid-phase reagent layer) onto a flow path member include a method of bringing the solid-phase reagent layer (or the release and solid-phase reagent layer) of the thermal transfer medium for a testing device into contact with a flow path member to transfer the solid-phase reagent layer (or the release and solid-phase reagent layer) onto the flow path member.

A printer used for the thermal transfer is not particularly limited and may be appropriately selected depending on the intended purpose. Examples of the printer include thermal printers equipped with, for example, a serial thermal head and line-type thermal head.

Energy applied for the thermal transfer is not particularly limited, may be appropriately selected depending on the intended purpose, and is preferably 0.05 mJ/dot or higher but 0.5 mJ/dot or lower. When the applied energy is 0.05 mJ/dot or higher, it is possible to efficiently melt the solid-phase reagent layer or the release and solid-phase reagent layer. When the applied energy is 0.5 mJ/dot or lower, it is possible to prevent the reagent from being thermally denatured. This prevents the support from being dissolved or the thermal head from being contaminated.

(Testing Device)

A testing device of the present invention includes a porous flow path member including a flow path through which an analyte is flowed, and a resin layer provided at at least one position on the flow path member, and further includes other members as needed.

A solid-phase reagent provided over a surface of the resin layer facing the flow path member contains an antibody.

The solid-phase reagent is covered with a protective layer containing a sugar.

The protective layer is the protective layer transferred from the thermal transfer medium for a testing device of the present invention.

In the testing device, the capture antibody is formed as a solid phase over the surface, facing the flow path member, of the resin layer that is provided at at least one position on the flow path member. This makes it possible to detect an analyte on the resin layer side. Therefore, as in existing enzyme-linked immunosorbent assay (ELISA) methods, a detecting portion can perform highly sensitive detection by means of the resin layer over which the capture antibody is formed as a highly dense solid phase. Meanwhile, as in existing immunochromatography methods, the testing liquid spreads through the flow path (flow path member) and undergoes reaction, being driven by a capillary action. This makes it possible to perform quick, highly sensitive measurement and obtain a definite judgment line.

Figure 2:
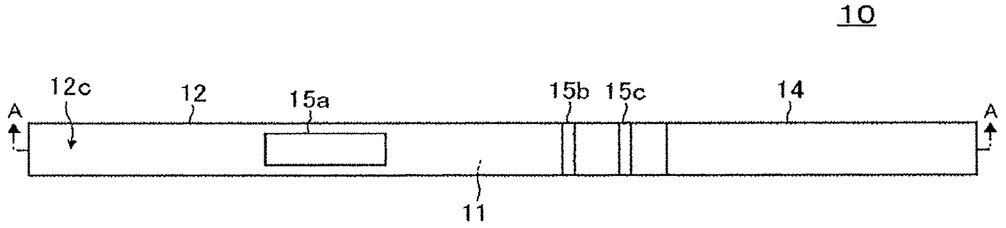
FIG. 2 is a top view of an example of a testing device according to an embodiment of the present invention.
Figure 3:
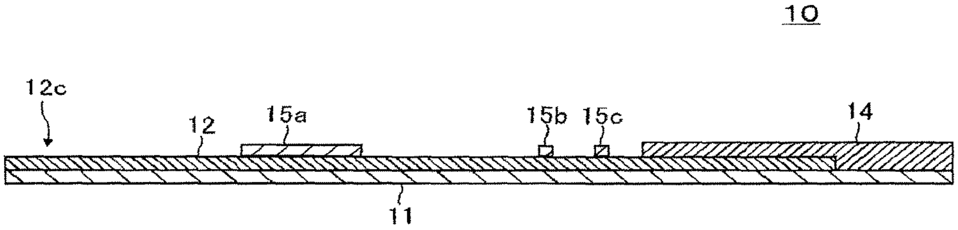
FIG. 3 is a cross-sectional view taken along a line A-A of FIG. 2.
Figure 4:
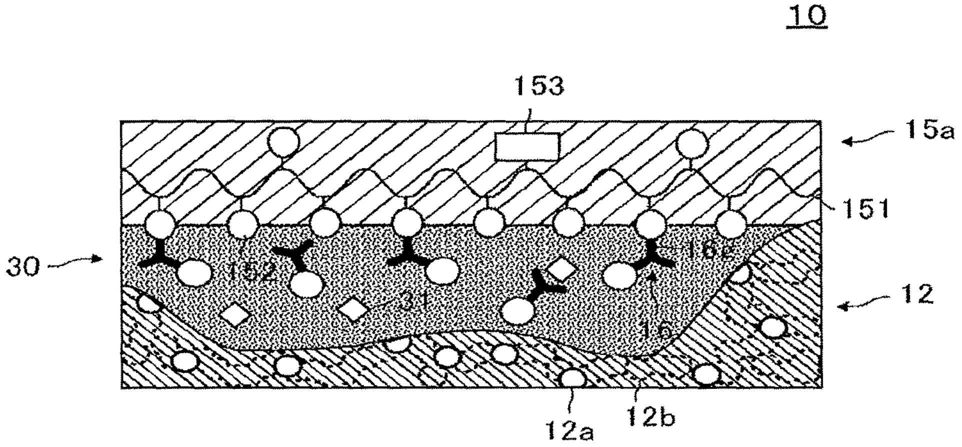
FIG. 4 is a schematic partial cross-sectional view of an example of a testing device, taken at a facing portion at which a flow path member and a resin layer face each other.

The testing device of the present invention will be described with reference to the drawings. FIG. 2 to FIG. 6B are drawings illustrating the overall configuration of the testing device. FIG. 2 is a top view of an example of the testing device according to an embodiment of the present invention. FIG. 3 is a cross-sectional view taken along a line A-A of the testing device of FIG. 2. FIG. 4 is a cross-sectional view of an example of the testing device, taken at a facing portion at which the flow path member and the resin layer face each other. FIG. 5A, FIG. 5B, FIG. 6A and FIG. 6B are cross-sectional views of other examples of the testing device, taken at a facing portion at which the flow path member and the resin layer face each other. In each drawing, the protective layer is not illustrated.

As illustrated in FIG. 2 to FIG. 6B, the testing device 10 includes: a porous flow path member 12 including a flow path through which a hydrophilic testing liquid 30 (an example of an analyte) such as blood, spinal fluid, urine, and an analyte extract liquid (e.g., a liquid containing an analyte collected with an analyte collecting unit such as a stick) is flowed; and resin layers (15*a*, 15*b*, and 15*c*) provided on the flow path member 12. A labeled antibody 16 reactive with an antigen contained in the testing liquid 30, a capture antibody 17 to capture the antigen, and a capture antibody (or antigen) 18 to capture the labeled antibody are formed as solid phases over surfaces of the resin layers (15*a*, 15*b*, and 15*c*) facing the flow path member 12, respectively. This makes it possible to adjust the intensity of interaction between the resin layers (15*a*, 15*b*, and 15*c*) and the reagents on a resin layer-by-resin layer basis for each of the resin layers (15*a*, 15*b*, and 15*c*). Therefore, even when an arbitrary flow path member 12 is selected depending on the intended purpose, it is easy to control release of the labeled antibody 16 and immobilization of the capture antibodies 17 and 18.

In the present embodiment, a case in which the testing device 10 includes the flow path member 12 over a base material 11, and an absorbing member 14 over the base material 11 and the flow path member 12 will be described. However, the present invention is not limited to this embodiment.

In the present embodiment, what is meant when it is said that something is provided over the flow path member 12 is that that something is provided in a manner to contact the flow path member 12 regardless of whether that something is above or below the flow path member 12 when the testing device 10 is set in place. When an arbitrary resin layer of the resin layers (15*a*, 15*b*, and 15*c*) is to be referred to, the arbitrary resin layer will be denoted as resin layer 15. The capture antibodies may be formed as solid phases by means of arbitrary chemical bonds such as covalent bond, hydrogen bond, and metallic bond or arbitrary interactions such as attaching, adhesion, adsorption, and van der Waals binding.

The description to follow is about a case in which the testing liquid 30 is a hydrophilic testing liquid such as blood, spinal fluid, urine, and an analyte extract liquid (e.g., a liquid containing an analyte collected with an analyte collecting unit such as a stick).

As illustrated in FIG. 4, in the testing device 10, the resin layer 15*a* (second resin layer) contains an amphiphilic resin 151 containing many hydrophilic groups 152. The amphiphilic resin 151 is preferably a main component (accounting for 50% by mass or greater) of the resin layer 15*a*.

A hydrophilic group is a group of atoms forming a weak bond with water molecules by, for example, hydrogen bond, and has affinity with water. Amphiphilicity means that a substance has affinity with both of water and organic solvents.

The labeled antibody 16 has a hydrophilic portion 16*g*, by which the labeled antibody 16 is formed as a solid phase over the surface of the resin layer 15*a* facing the flow path member 12. Meanwhile, when the gap formed in the facing portion at which the flow path member 12 and the resin layer 15*a* face each other is filled with the testing liquid 30, the hydrophilic portion 16*g* of the labeled antibody 16 comes to have affinity with the hydrophilic testing liquid 30 to cause the labeled antibody 16 to be released from the amphiphilic resin 151. When the testing liquid contains an antigen 31, the released labeled antibody 16 and the antigen 31 react and bind with each other by an antigen-antibody reaction. In order to prevent inhibition against binding of the antigen and the antibody, it is preferable that the amphiphilic resin 151 be a water-insoluble resin.

Water-insolubility means substantial water-insolubility. Substantial water-insolubility means that a resin undergoes a mass change in an amount of 1% by mass or less when immersed in a large amount of water at 25 degrees C. for 24 hours and then sufficiently dried by a method such as vacuum drying. The reason why such a resin is substantially water-insoluble is that the mass change is attributed to mass reduction due to leaching of a by-product (e.g., a monomer component) contained in the resin product into the water.

Figure 5A:
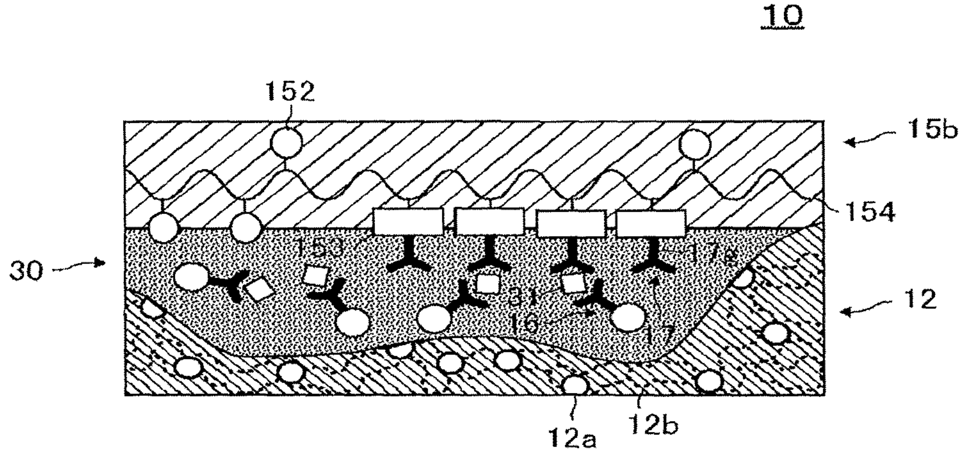
FIG. 5A is a schematic partial cross-sectional view of another example of a testing device, taken at a facing portion at which a flow path member and a resin layer face each other.
Figure 5B:
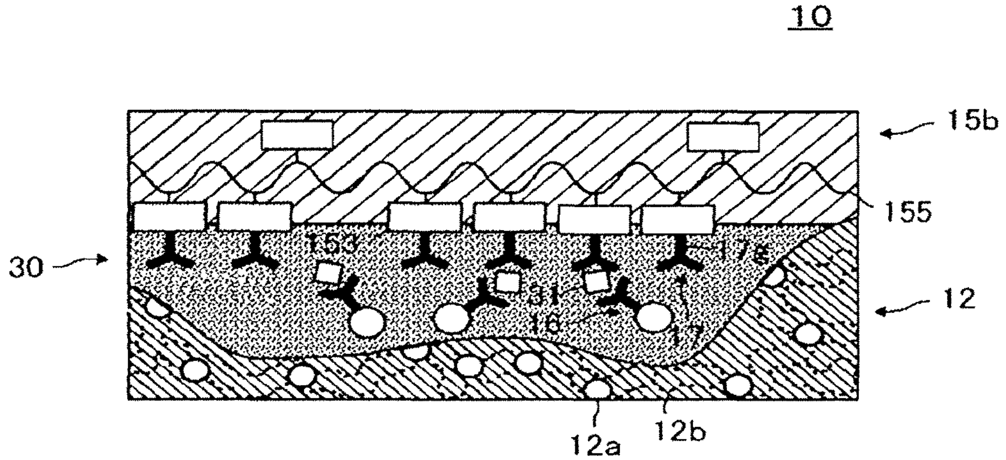
FIG. 5B is a schematic partial cross-sectional view of another example of a testing device, taken at a facing portion at which a flow path member and a resin layer face each other.

As illustrated in FIG. 5A and FIG. 5B, in the testing device 10, it is preferable that the resin layer 15*b* (first resin layer) be a resin containing a hydrophobic group 153. Specifically, the resin layer 15*b* contains a hydrophobic resin 155 or an amphiphilic resin 154 containing many hydrophobic groups 153. The hydrophobic resin 155 or the amphiphilic resin 154 is preferably a main component (accounting for 50% by mass or greater) of the resin layer 15*b*.

A hydrophobic group is a group of atoms that has a poor intimacy with water or a poor affinity with water and is sparingly soluble in water or sparingly miscible with water.

The capture antibody 17 has a hydrophobic portion 17*g*. The capture antibody 17 is formed as a solid phase over a surface of the resin layer 15*b* facing the flow path member 12, by the hydrophobic portion 17*g* binding with that surface by an intermolecular force. When the gap formed in the facing portion at which the flow path member 12 and the resin layer 15*b* face each other is filled with the testing liquid 30, the capture antibody 17 captures the antigen 31 that is in the state of being bound with the labeled antibody 16. As a result, the antigen 31 and the labeled antibody 16 are immobilized and develop a color. Therefore, the resin layer 15*b* can be used as a line for judging presence or absence of the antigen 31. In order to prevent feathering of the line, it is preferable that the hydrophobic resin 155 and the amphiphilic resin 154 be both water-insoluble resins.

Figure 6A:
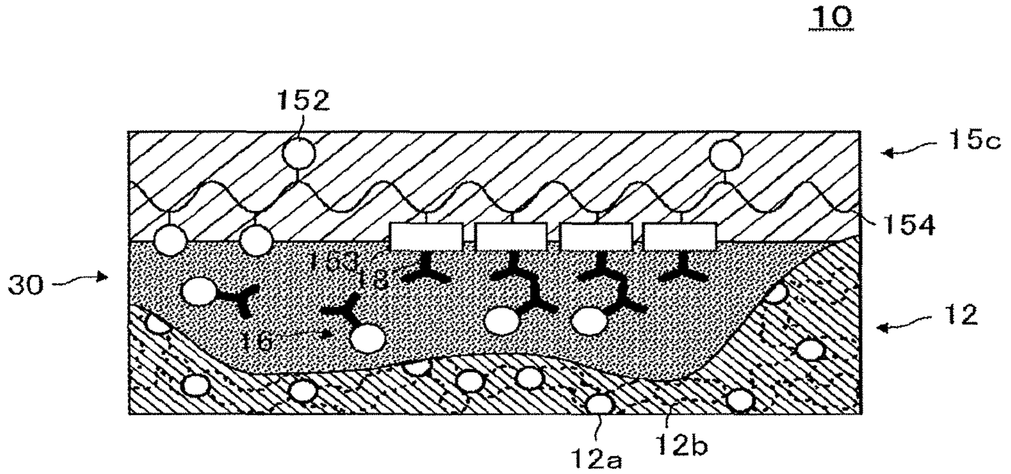
FIG. 6A is a schematic partial cross-sectional view of another example of a testing device, taken at a facing portion at which a flow path member and a resin layer face each other.
Figure 6B:
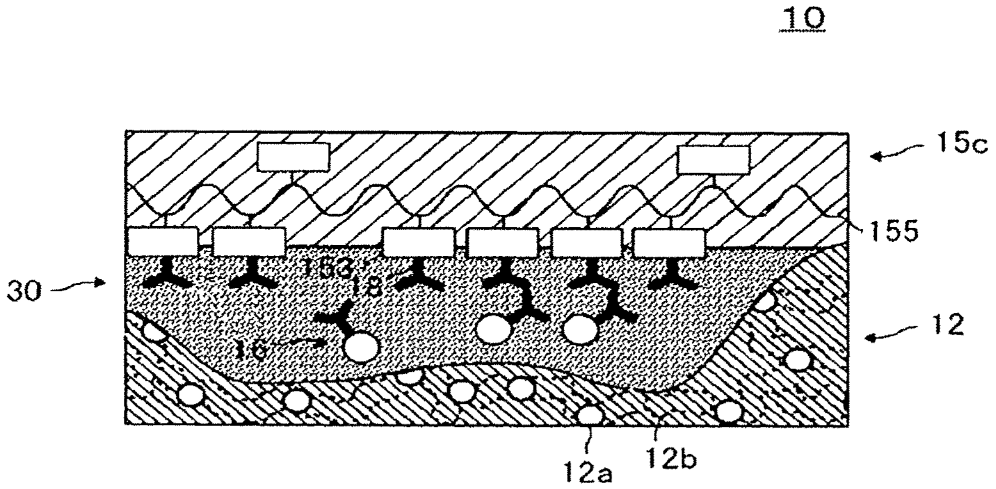
FIG. 6B is a schematic partial cross-sectional view of another example of a testing device, taken at a facing portion at which a flow path member and a resin layer face each other.

As illustrated in FIG. 6A and FIG. 6B, in the testing device 10, the resin layer 15*c* (first resin layer) contains a hydrophobic resin 155 or an amphiphilic resin 154 containing many hydrophobic groups 153. The hydrophobic resin 155 or the amphiphilic resin 154 is preferably a main component (accounting for 50% by mass or greater) of the resin layer 15*c*.

The capture antibody 18 is formed as a solid phase over a surface of the resin layer 15*c* facing the flow path member 12, by a hydrophobic portion of the capture antibody 18 binding with that surface by an intermolecular force. The capture antibody 18 is not particularly limited and may be appropriately selected depending on the intended purpose, so long as the capture antibody 18 can capture the labeled antibody 16. Examples of the capture antibody 18 include an antibody that specifically binds with the labeled antibody 16. Hence, the labeled antibody 16 is immobilized and develops a color. Therefore, the resin layer 15*c* can be used as a control line for indicating that the labeled antibody 16 has arrived. In order to prevent feathering of the control line, it is preferable that the hydrophobic resin 155 and the amphiphilic resin 154 be both water-insoluble resins.

The resin layers are preferably non-porous bodies. The non-porous body refers to a non-porous structure substantially free of voids, and a structure opposed to a porous material such as a membrane that contains voids provided for promoting absorption of a liquid. Hence, a material that contains only few cells that have been incidentally mixed in the material during a production process and that do not contribute to promotion of the liquid absorbing action is encompassed within the non-porous body.

Next, characteristics attributed to the resin layer being a non-porous body will be described.

Hitherto, test lines and control lines have been formed by directly coating a liquid in which a capture antibody is dissolved over the flow path member formed of a hydrophilic porous material. Hence, the capture antibody is diffused inside the porous material along with permeation of the liquid. However, a color developed by labeling particles such as gold colloid particles to be bound with the capture antibody present inside the porous material cannot actually be sensed due to light scattering. This means that most of the capture antibody is not used effectively.

Generally, color developing particles that can be sensed from the porous material are particles that are present at and above the depth of about 5 μm from the surface of the porous material. In order to immobilize the capture antibody needed for testing to the region at and above the depth of 5 μm, there is a need for coating the capture antibody in a large amount considering diffusion of the capture antibody in the direction of thickness. That is, the amount of the capture antibody to be coated increases in proportion to the thickness of the porous material.

In the present invention, the resin layer formed of a non-porous body containing many hydrophobic groups is used for immobilization of the capture antibody. Therefore, the capture antibody is immobilized to only the surface of the resin layer without entering the inside of the resin layer. A color is developed when labeling particles bind with the capture antibody immobilized to the surface of the resin layer. The color can be sensed through the resin layer formed of the non-porous body that does not scatter light. This significantly improves the efficiency of utilization of the color developed by the labeling particles. Because there are no wasteful color developing particles in the direction of thickness, there is an advantage that the amount of the capture antibody coated can be significantly saved. For example, when it is assumed that the thickness of the flow path member formed of the hydrophilic porous material is 100 μm and color development from a region at and above the depth of 5 μm from the surface of the flow path member can only be utilized, the amount of the capture antibody coated used for obtaining color development of the same intensity can be reduced to 1/20.

In the present invention, the resin layer formed of a non-porous body containing many hydrophobic groups is used for immobilization of the capture antibody. Therefore, the efficiency of utilization of the color developed by the labeling particles can be improved significantly, and the amount of the capture antibody coated can be reduced from the amount used in existing devices because there are no wasteful color developing particles in the direction of thickness.

In the present embodiment, the testing device 10 configured to test presence or absence of an antigen 31 in the testing liquid 30 is described. However, the testing device of the present invention is not limited to a testing device utilizing an antigen-antibody reaction. For example, the testing device may be configured to test a specific component in the testing liquid 30 by using, as a reagent, a reagent that changes hues upon a structural change.

Each member constituting the testing device 10 will be described in detail below.

<Base Material>

The base material 11 is not particularly limited and may be appropriately selected depending on the intended purpose. Examples of the base material include organic, inorganic, and metallic base materials.

The base material 11 is not particularly limited and may be appropriately selected depending on the intended purpose. However, it is preferable that at least one surface of the base material 11 be coated with a hydrophobic resin.

When the testing device 10 is used as a sensor chip, it is preferable to use a light-weight, flexible, and inexpensive synthetic resin as the base material 11.

In the present embodiment, it is optional to select a base material 11 having a high durability such as a plastic sheet. This improves the durability of the testing device 10 as a result.

A constituent material of the base material 11 is not particularly limited and may be appropriately selected depending on the intended purpose. Examples of the constituent material of the base material 11 include polyvinyl chlorides, polyethylene terephthalates, polypropylenes, polystyrenes, polyvinyl acetates, polycarbonates, polyacetals, modified polyphenyl ethers, polybutylene phthalates, and ABS resins. Among these materials, polyethylene terephthalates are preferable because polyethylene terephthalates are low-price and highly versatile.

The shape of the base material 11 is not particularly limited and may be appropriately selected depending on the intended purpose. However, a sheet shape is preferable.

The average thickness of the base material 11 is not particularly limited, may be appropriately selected depending on the intended purpose, and is preferably 0.01 mm or greater but 0.5 mm or less. When the average thickness of the base material 11 is 0.01 mm or greater, the base material 11 has an adequate strength as a base material. When the average thickness of the base material 11 is 0.5 mm or less, the base material has a good flexibility and is suitable as a sensor.

The average thickness may be an average of thicknesses measured with a micrometer (MDH-25M available from Mitutoyo Corporation) at a total of 15 positions of a measuring target, namely 5 positions in the longer direction×3 positions in the width direction that are selected at approximately equal intervals. In the present embodiment, the thickness may be a length of a target in a direction perpendicular to a contact plane at which the base material 11 and the flow path member 12 contact each other.

<Flow Path Member>

The flow path member 12 of the testing device 10 is not particularly limited and may be appropriately selected depending on the intended purpose so long as the flow path member is a member through which the testing liquid 30 can be flowed. Examples of the flow path member 12 include a hydrophilic porous material.

The flow path member 12 formed of the hydrophilic porous material contains voids (12*a* and 12*b*), and a flow path is formed when the testing liquid 30 flows through the voids (12*a* and 12*b*).

In FIG. 4 to FIG. 6, the void 12*a* is a void formed in the cross-sections, and the void 12*b* is a void present more backward in the cross-sections. It is preferable that cells be present in the hydrophilic porous material and that the cells be linked together to form a continuous cell.

The continuous cell is distinguished from independent cells that are not linked together. The continuous cell has a function of sucking in a liquid by a capillary action or letting a gas pass through the continuous cell because the continuous cell has small holes in the walls between the cells. The flow path member 12 needs no external actuating device such as a pump because the flow path member 12 is configured to deliver the testing liquid 30 by utilizing a capillary action through the voids (12*a* and 12*b*).

The hydrophilic porous material is not particularly limited and may be appropriately selected depending on the intended purpose. However, a material having hydrophilicity and a high voidage is preferable.

The hydrophilic porous material refers to a porous material that is easily permeable by an aqueous solution. The hydrophilic porous material is referred to as being easily permeable when in a water permeability evaluation test in which 0.01 mL of pure water is dropped onto a surface of a plate-shaped test piece of the hydrophilic porous material dried at 120° C. for 1 hour, the whole of 0.01 mL of the pure water permeates the test piece in 10 minutes.

The voidage of the hydrophilic porous material is not particularly limited, may be appropriately selected depending on the intended purpose, and is preferably 40% or higher but 90% or lower and more preferably 65% or higher but 80% or lower. When the voidage of the hydrophilic porous material is 90% or lower, the flow path member has a good strength. When the voidage of the hydrophilic porous material is 40% or higher, permeability of the testing liquid is good.

The voidage of the hydrophilic porous material can be calculated according to a calculation formula 1 below based on a basis weight ($g/m^2$) and a thickness (μm) of the hydrophilic porous material and the specific gravity of the component of the hydrophilic porous material.

Voidage (%)={1−[basis weight ($g/m^2$)/thickness (μm)/specific gravity of the component]}×100 [Calculation formula 1]

The hydrophilic porous material is not particularly limited and may be appropriately selected depending on the intended purpose. Examples of the hydrophilic porous material include filter paper such as membrane film, plain paper, high-quality paper, watercolor paper, Kent paper, synthetic paper, synthetic resin film, special-purpose paper with a coat layer, fabric, fiber product, film, inorganic substrate, and glass. One of these hydrophilic porous materials may be used alone or two or more of these hydrophilic porous materials may be used in combination. Among these hydrophilic porous materials, filter paper such as membrane film and fabric are preferable, and filter paper such as membrane film is more preferable because filter paper has a high voidage and a good hydrophilicity.

Examples of the fabric include artificial fiber such as rayon, bemberg, acetate, nylon, polyester, and vinylon, natural fiber such as cotton and silk, blended fabric of these fibers, or non-woven fabric of these fibers.

The shape of the hydrophilic porous material is not particularly limited and may be appropriately selected depending on the intended purpose. However, a sheet shape is preferable.

The average thickness of the hydrophilic porous material is not particularly limited, may be appropriately selected depending on the intended purpose, and is preferably 0.01 mm or greater but 0.3 mm or less. When the average thickness of the hydrophilic porous material is 0.01 mm or greater, the flow path member has a good strength. When the average thickness of the hydrophilic porous material is 0.3 mm or less, the amount of the testing liquid needed can be optimized.

<Resin Layer>

The function of the resin layer 15 will be described based on comparison with an existing testing device illustrated in FIG. 7 and FIG. 8.

Figure 7:
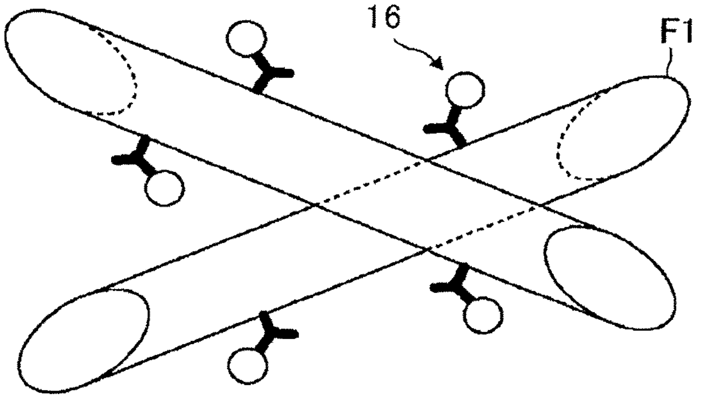
FIG. 7 is a conceptual diagram of a conjugate pad of an existing testing device.

FIG. 7 is a conceptual diagram of a conjugate pad of an existing testing device. FIG. 8 is a conceptual diagram of a membrane of an existing testing device.

In the existing testing device, when the conjugate pad has an extremely high hydrophilicity, a testing liquid tends to stay within the conjugate pad and does not easily flow into the membrane. Conversely, when the conjugate pad has an extremely high hydrophobicity, the testing liquid smoothly flows into the membrane, but a long time is needed for testing or the testing liquid is needed in a large amount because the conjugate pad has a poor absorbency for absorbing the testing liquid from the sample pad. Hence, fiber F1 usable for the conjugate pad is limited. Furthermore, in the existing testing device, the labeled antibody 16 is formed as a solid phase on the fiber F1 constituting the conjugate pad (see FIG. 7). The labeled antibody 16 can be released from the conjugate pad only when the labeled antibody 16 has a weak force of binding with the fiber F1. That is, as a matter of design, the existing testing device is limited in the fiber F1 and labeled antibody 16 that can be used.

Figure 8:
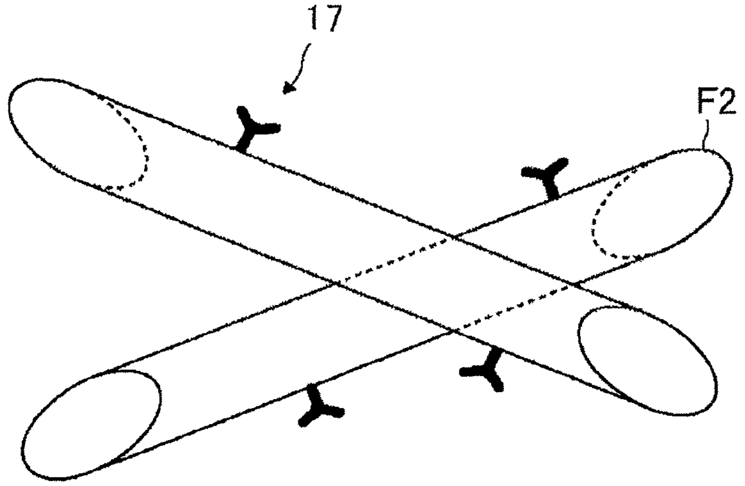
FIG. 8 is a conceptual diagram of a membrane of an existing testing device.

Likewise, in the existing testing device, the capture antibody 17 is formed as a solid phase on fiber F2 constituting the membrane (see FIG. 8). Hence, the capture antibody 17 can be immobilized to the membrane only when the capture antibody 17 has a strong force of binding with the fiber F2. That is, as a matter of design, the existing testing device is limited in the fiber F2 and capture antibody 17 that can be used.

In the testing device 10 according to the present embodiment, the reagents such as the labeled antibody 16, the capture antibody 17, and the capture antibody 18 are formed as solid phases over the resin layers 15 (15*a*, 15*b*, and 15*c*). Hence, release of the labeled antibody or immobilization of the capture antibodies can be controlled based on the intensity of interaction between the resin layers 15 and the capture antibodies and affinity with the testing liquid 30.

As the method for adjusting the intensity of interaction between the resin layers 15 and the capture antibodies and affinity with the testing liquid 30, for example, there is a method of changing the kinds of the resins to constitute the resin layers 15 or the composition ratios of the resins in a manner to match the corresponding capture antibodies. For example, the higher the hydrophobic percentage in the resin constituting the resin layer 15, the easier it is to immobilize a capture antibody containing a hydrophobic group to the resin layer 15 based on hydrophobic interaction.

The hydrophobic interaction refers to a cause (driving force) of a change occurring in water that hydrophobic molecules or hydrophobic groups immiscible with water aggregate with each other. To be more specific, when hydrophobic molecules or molecules having hydrophobic groups are put in water, in many cases, these molecules not only simply do not dissolve but come into a state of the hydrophobic molecules and the hydrophobic groups contacting each other to reduce the area of contact with water molecules as much as possible. The hydrophobic interaction refers to a consequent phenomenon that the hydrophobic molecules attract each other and seem to have a binding force acting between the molecules.

When the hydrophilic percentage is high in the resin constituting the resin layer 15, the resin layer 15 has a strong interaction with a hydrophilic capture antibody. However, it is estimated that when the bonding portion between the resin layer and the capture antibody contacts the testing liquid 30, the reagent comes to have affinity with the testing liquid 30 and is easily released into the testing liquid 30.

The resin constituting the resin layer 15 is preferably a water-insoluble resin. A water-insoluble resin, when used in the resin layer, can be prevented from being dissolved in the testing liquid 30 and hence clogging the flow path or smudging the control line or the test line.

The amphiphilic resin constituting the resin layer 15*a* is not particularly limited and may be appropriately selected depending on the intended purpose. Examples of the amphiphilic resin include polyvinyl alcohols, polyvinylacetal resins, polyacrylic acids, polyacrylic acid-acrylonitrile copolymers, vinyl acetate-acrylic acid ester copolymers, acrylic acid-acrylic acid ester copolymers, styrene-acrylic acid copolymers, styrene-methacrylic acid copolymers, styrene-methacrylic acid-acrylic acid ester copolymers, styrene-α-methylstyrene-acrylic acid copolymers, styrene-α-methylstyrene-acrylic acid-acrylic acid ester copolymers, styrene-maleic acid copolymers, styrene-maleic anhydride copolymers, vinyl naphthalene-acrylic acid copolymers, vinyl naphthalene-maleic acid copolymers, vinyl acetate-maleic acid ester copolymers, vinyl acetate-crotonic acid copolymers, vinyl acetate-acrylic acid copolymers, and salts of these amphiphilic resins. One of these amphiphilic resins may be used alone or two or more of these amphiphilic resins may be used in combination.

Among these amphiphilic resins, copolymers of hydrophobic functional group-containing monomers and hydrophilic functional group-containing monomers and polymers formed of monomers having both of hydrophobic functional groups and hydrophilic functional groups are preferable.

As the form of the copolymers, any of random copolymers, block copolymers, alternating copolymers, and graft copolymers may be used.

Examples of the hydrophobic resin constituting the resin layer 15*b* and the resin layer 15*c* include polystyrene-based resins such as polystyrenes and acrylonitrile-butadiene-styrene copolymers, polyolefin-based resins or cyclic polyolefin-based resins such as polypropylene resins, polyethylene resins, and ethylene-propylene copolymers, polycarbonate resins, polyethylene terephthalate resins, methacrylic-based resins such as polymethylmethacrylate resins, vinyl chloride resins, polybutylene terephthalate resins, polyarylate resins, polysulfone resins, polyether sulfone resins, polyether ether ketone resins, polyether imide resins, fluororesins such as polytetrafluoroethylene, polymethylpentene resins, acrylic-based resins such as polyacrylonitrile, and cellulose-based resins such as propionate resins. One of these hydrophobic resins may be used alone or two or more of these hydrophobic resins may be used in combination.

Examples of compounds that may constitute the resin layer 15*b* and the resin layer 15*c* other than the hydrophobic resins include: natural waxes such as beeswax, carnauba wax, cetaceum, Japan wax, candelilla wax, rice bran wax, and montan wax; synthetic waxes such as paraffin wax, microcrystalline wax, oxidized wax, ozokerite, ceresin, ester wax, polyethylene wax, and polyethylene oxide wax; higher fatty acids such as margaric acid, lauric acid, myristic acid, palmitic acid, stearic acid, furoic acid, and behenic acid; higher alcohols such as stearic alcohol and behenyl alcohol; esters such as fatty acid ester of sorbitan; and amides such as stearin amide and oleic amide. One of these compounds may be used alone or two or more of these compounds may be used in combination.

Among the compounds that may constitute the resin layer 15*b* and the resin layer 15*c*, polystyrene resins, polyolefin resins, carnauba wax, and polyethylene wax are preferable because these compounds have a strong hydrophobic interaction.

The resins constituting the resin layers (15*a*, 15*b*, and 15*c*) may be the same resin. In this case, it is preferable that the resin constituting the resin layer 15*a* be higher in hydrophilicity than the resins constituting the resin layers (15*b* and 15*c*). Note that the same resin can be said to have a higher hydrophilicity when the percentage of hydrophilic groups is higher, without the need for measuring hydrophilicity.

The labeled antibody 16 to be formed as a solid phase over the resin layer 15*a* is not particularly limited and may be appropriately selected depending on the intended purpose, so long as the labeled antibody 16 has a hydrophilic portion and is reactive with the antigen 31. Examples of the labeled antibody 16 include gold colloid-labeled antibodies such as gold colloid-labeled anti-human IgG, labeled antibodies against various allergens, and particles for labeling other antibodies.

The particles for labeling other antibodies are not particularly limited to gold colloid and may be appropriately selected depending on the intended purpose. Examples of such particles include metal colloids other than gold colloid, enzymatic labeling particles containing an enzyme, coloring particles containing a pigment, fluorescent particles containing a fluorescent substance, and magnetic body encapsulating particles containing a magnetic body. One of these kinds of particles may be used alone or two or more of these kinds of particles may be used in combination.

The antibody may be any form among monoclonal antibody, polyclonal antibody, chimeric antibody, Fab antibody, and $(Fab)_2$ antibody.

The capture antibody 17 to be formed as a solid phase over the resin layer 15*b* is not particularly limited and may be appropriately selected depending on the intended purpose, so long as the capture antibody 17 has a hydrophobic portion and is reactive with the antigen 31. Examples of the capture antibody 17 include antibodies such as anti-human IgG and antibodies against various allergens.

The antibody may be any form among monoclonal antibody, polyclonal antibody, chimeric antibody, Fab antibody, and $(Fab)_2$ antibody.

The capture antibody 18 to be formed as a solid phase over the resin layer 15*c* is not particularly limited and may be appropriately selected depending on the intended purpose, so long as the capture antibody 18 has a hydrophobic group and is reactive with the labeled antibody 16. Examples of the capture antibody 18 include antibodies such as human IgG against the labeled antibody 16 and antibodies raised as examples above.

The method for forming the reagents such as the labeled antibody 16 and the capture antibodies (17 and 18) as solid phases over the resin layers 15 is not particularly limited and may be appropriately selected depending on the intended purpose. Examples of the method include a method of coating a solution containing a reagent such as a capture antibody over the resin layer 15 and then drying up the solution by fast drying, and a method of coating a solution containing a reagent over the resin layer 15, leaving the coated resin layer standing still (for incubation) in a high humidity environment so as not for the coating liquid to dry, cleaning away any other components than the antibody such as an inorganic salt with, for example, distilled water, and then drying the antibody.

The method for treating a reagent such as the capture antibody as a coating liquid is not particularly limited and may be appropriately selected depending on the intended purpose. However, typically, it is preferable to dilute the reagent with a buffer solution (buffering agent) called buffer.

The buffer solution is not particularly limited and may be appropriately selected depending on the intended purpose, so long as the buffer solution is a buffer that does not inhibit antigen-antibody reaction of the capture antibody. Examples of the buffer solution include buffer solutions commonly used for diluting antibodies. The buffer solution may be, for example, phosphate buffered saline (PBS), trishydroxymethylaminomethane (Tris)-HCl, and good buffer. Among these buffer solutions, phosphate buffered saline (PBS) and good buffer are preferable.

The phosphate buffered saline (PBS) has pH of preferably from 4 through 10 and more preferably from 6 through 8. The composition of the PBS is not particularly limited and there are various compositions of PBS. As an example of the composition of the PBS, there is a composition in which NaCl is 8.0 g/L, KCl is 0.2 g/L, $NaH_2PO_4$ is 1.44 g/L, and $KH_2PO_4$ is 0.24 g/L. There are also compositions free of potassium and compositions containing calcium and magnesium.

Examples of the good buffer include 2-(N-monopholino) ethanesulfonic acid (MES) and N-2-hydroxyethylpiperazine-2-sulfonic acid (HEPES).

After the reagents such as the capture antibodies (17 and 18) are formed as solid phases over the resin layers 15, protective layers are provided over the reagents (capture antibodies) in a manner to cover the reagents. This makes it possible to sustain the functional activities of the capture antibodies for a long term and suppress functional degradation of the capture antibodies due to, for example, physical frictions.

The protective layer is present in a manner to cover the whole of the reagent (capture antibody), and has a role of sustaining the function and the structure.

The capture antibody is typically formed of amino acid. Amino acid contains a hydrophobic group and a hydrophilic group and can be present most stably in a low-temperature liquid environment. In a body or in a buffer, the capture antibody retains a stable structure with a hydrophilic group present over a surface of the capture antibody and a hydrophobic group present inside the capture antibody. However, when the capture antibody (17 or 18) is formed as a solid phase over the resin layer 15 and dried, the capture antibody spontaneously attempts to obtain a stable structure adapted to the dry state. Hence, the hydrophilic group present externally in the first place goes inside and the hydrophobic group goes outside to collapse the structure, resulting in degradation of stability of the capture antibody or functional loss of the capture antibody. When a protective layer covers the capture antibody in order to suppress the structure from collapse, the material in the protective layer brings the capture antibody into an apparent hydration state. This makes it possible for the capture antibody to be formed as a solid phase over the resin layer 15 while being kept in a stable structure without collapse of the structure of the capture antibody.

In the present embodiment, it is preferable that the resin layer 15 be secured over the flow path member 12.

The method for securing the resin layer 15 over the flow path member 12 is not particularly limited and may be appropriately selected depending on the intended purpose, so long as the method secures the resin layer 15 in a manner that the reagent and the testing liquid 30 can contact each other during testing. Examples of the method include a method of thermally transferring the resin to constitute the resin layer onto the flow path member 12 with, for example, a thermal transfer printer, a method of transferring the resin to constitute the resin layer with a pressure applied with, for example, a dot impact printer, and a method of pasting the resin to constitute the resin layer over the flow path member 12 with, for example, a tape, an adhesive, or a tackifier.

<Absorbing Member>

The absorbing member 14 is not particularly limited so long as the absorbing member 14 is a member configured to absorb water, and may be appropriately selected from known materials.

Examples of the absorbing member 14 include fiber such as paper and cloth, polymer compounds containing a carboxyl group or a salt of a carboxyl group, partially cross-linked bodies of polymer compounds containing a carboxyl group or a salt of a carboxyl group, and partially cross-linked bodies of polysaccharides.

<Other Members>

The other members are not particularly limited and may be appropriately selected depending on the intended purpose. Examples of the other members include a protective member, a labeled antibody support pad, and a sample dropping pad.

The protective member is a member intended for preventing contamination of a hand that touches the flow path member.

The protective member is not particularly limited and may be appropriately selected depending on the intended purpose. Examples of the protective member include a housing configured to cover the testing device on the whole and a film provided over the flow path member.

When providing the protective member, it is preferable that an opening be provided in the protective member at a position to be above the dropping portion of the flow path member 12. It is preferable that an opening be provided in the protective member in order to release pressure in the flow path.

—Applications of Testing Device—

Applications of the testing device 10 are not particularly limited and may be appropriately selected depending on the intended purpose. Examples of the applications include biochemical sensors (sensing chips) for blood testing and DNA testing, and small-size analytical devices (chemical sensors) for quality control of foods and beverages, etc.

Samples (analytes) used in biochemical testings are not particularly limited and may be appropriately selected depending on the intended purpose. Examples of the samples include pathogens such as bacteria and viruses, and blood, saliva, lesional tissues, etc. separated from living organisms, or excretion such as enteruria. For performing a prenatal diagnosis, the sample may be a part of a fetus cell in an amniotic fluid or a part of a dividing egg cell in a test tube. These samples may be condensed to a sediment directly or by, for example, centrifugation as needed and then subjected to a pre-treatment for cell destruction by, for example, an enzymatic treatment, a thermal treatment, a surfactant treatment, an ultrasonic treatment, and any combinations of these treatments.

The testing device 10 according to the present embodiment also has a function of chromatographing (separating or refining) a testing liquid because the flow path member 12 functions as a static bed. In this case, the flow path member 12 including the continuous cells of which internal wall has hydrophilicity functions as the static bed (or a support). Different components in the testing liquid flow through the flow path at different speeds because of the difference in the interaction with the static bed during the process of permeating the flow path, i.e., the difference in whether the components are hydrophilic or hydrophobic.

A component having a higher hydrophilicity adsorbs to the porous portion functioning as the static bed more easily, and repeats adsorbing and desorbing more times, resulting in a lower speed of permeation through the flow path. In contrast, a component having a higher hydrophobicity permeates the flow path without adsorbing to the static bed, and hence moves through the flow path more quickly. By extracting the target component in the testing liquid 30 selectively based on the difference in the moving speed in the testing liquid and allowing the target component to undergo a reaction, it is possible to use the testing device 10 as a highly functional chemical or biochemical sensor.

<Testing Method>

A testing method relating to the present invention is not particularly limited and may be appropriately selected depending on the intended purpose. The testing method includes a step of supplying a hydrophilic testing liquid to the flow path member 12 of the testing device 10 and a step of bringing the labeled antibody 16 (an example of a reagent) formed as a solid phase over the resin layer 15*a* into contact with the testing liquid 30 to release the labeled antibody 16 from the resin layer 15*a*. The testing method further includes other steps as needed.

A testing method using the testing device 10 may include a step of supplying the testing liquid 30 to the flow path member 12 of the testing device 10 and a step of making the capture antibody 17 formed as a solid phase over the resin layer 15*b* capture an antigen 31 (an example of a part of an analyte) when any antigen 31 is contained in the testing liquid 30.

In a specific operation, the hydrophilic testing liquid 30 is dropped and supplied onto a dropping portion 12*c* (see FIG. 2) provided on the flow path member 12 of the testing device 10. Next, the supplied testing liquid 30 and the labeled antibody 16 formed as a solid phase over the resin layer 15*a* are brought into contact with each other, to release the labeled antibody 16 from the resin layer 15*a*. When any antigen 31 is contained in the testing liquid 30, the labeled antibody 16 released from the resin layer 15*a* reacts and binds with the antigen 31 (see FIG. 4).

Next, the testing liquid 30 containing the labeled antibody 16 and the antigen 31 spreads along the flow path member 12 and arrives at the region at which the resin layer 15*b* is disposed. The capture antibody 17 formed as a solid phase over the surface of the resin layer 15*b* facing the flow path member 12 binds with and captures the antigen 31 that is in the state of being bound with the labeled antibody 16. The capture antibody 17 is formed as a solid phase over the resin layer 15*b* by the hydrophobic group 17*g*. Therefore, even when the capture antibody 17 contacts the testing liquid 30, the capture antibody 17 does not come to have affinity with the testing liquid 30 and is not easily released into the testing liquid 30. Even if some part of the capture antibody 17 is released into the testing liquid 30, the released part gets bound with the fibers constituting the flow path member 12 soon. This facilitates immobilization of the labeled antibody 16 to about the resin layer 15*b*, resulting in a clear color development on the test line (see FIG. 5A and FIG. 5B).

Any labeled antibody 16 that passes by the resin layer 15*b* without being captured spreads along the flow path member 12 and arrives at the region at which the resin layer 15*c* is disposed. In the present embodiment, the capture antibody 18 containing a hydrophobic group is formed as a solid phase over the surface of the resin layer 15*c* facing the flow path member 12. The labeled antibody 16 is captured by being bound with the capture antibody 18.

The capture antibody 18 is formed as a solid phase over the resin layer 15*c* by the hydrophobic group. Therefore, even when the capture antibody 18 contacts the testing liquid 30, the capture antibody 18 does not come to have affinity with the testing liquid 30 and is not easily released into the testing liquid 30. Even if some part of the capture antibody 18 is released into the testing liquid 30, the released part gets bound with the fibers constituting the flow path member 12 soon. This facilitates immobilization of the labeled antibody 16 to about the resin layer 15*c*, resulting in a clear color development on the control line (see FIG. 6A and FIG. 6B).

(Testing Kit)

A testing kit of the present invention includes the testing device of the present invention, and at least one selected from the group consisting of an analyte collecting unit configured to collect an analyte and a liquid for treating the analyte, and further includes other members as needed.

Figure 9:
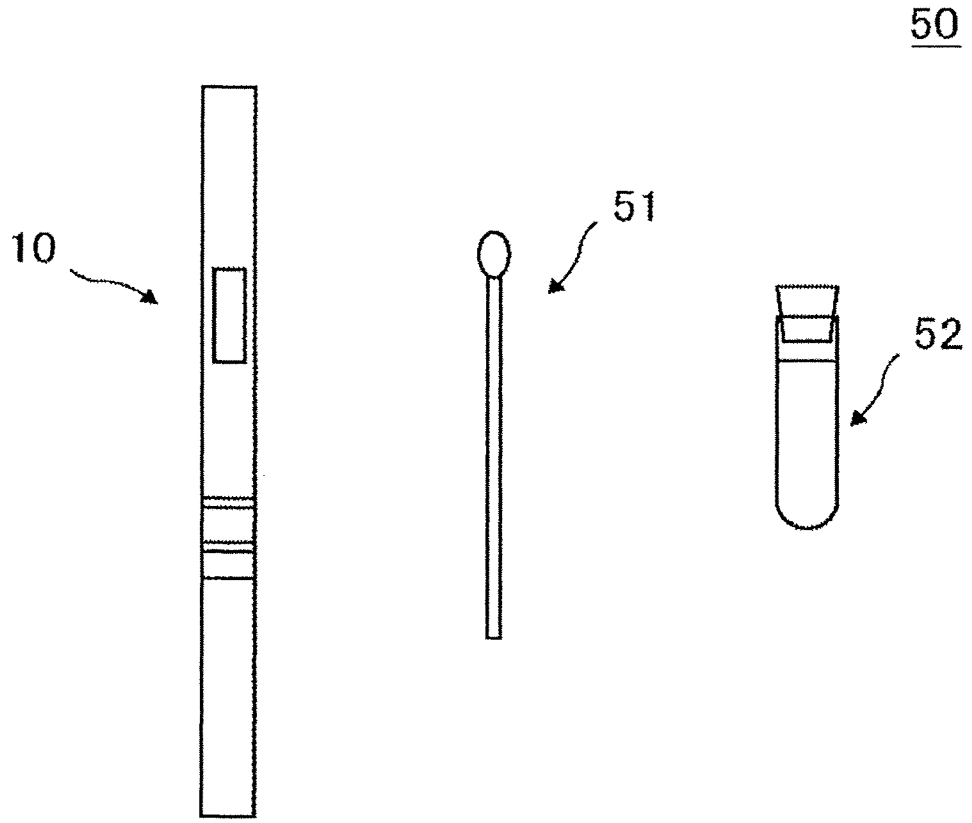
FIG. 9 is a conceptual diagram of an example of a testing kit according to an embodiment of the present invention.

As illustrated in FIG. 9, the testing kit includes the testing device 10 of the present invention and at least one of a tool configured to collect an analyte (an example of the analyte collecting unit) and a liquid for treating the analyte.

Examples of the tool configured to collect an analyte include a sterilized cotton swab 51 for collecting an analyte from, for example, pharynx or nasal cavity.

Examples of the liquid for treating the analyte include a diluting fluid 52 for diluting the analyte and an extraction liquid for extracting the analyte.

Examples of the other members include an instruction manual.

In the embodiment described above, a case where the reagents formed as solid phases over the resin layers 15 are an antigen or an antibody is described. The present invention is not limited to this embodiment. The present invention can also be applied to, for example, a testing device using an indicator used in a chemical assay.

The indicator used in a chemical assay refers to a reagent for indicating a chemical property of a solution. The indicator is not particularly limited and may be appropriately selected depending on the intended purpose. Examples of the indicator include a pH indicator, various ionophores that discolor by reacting with various ions such as a lead ion, a copper ion, and a nitrite ion, and reagents that discolor by reacting with various agricultural chemicals.

In the embodiment described above, a case where the protective layer 106 and solid-phase reagent layer 103 of the thermal transfer medium 100 for a testing device, or the protective layer 106 and release and solid-phase reagent layer 105 of the thermal transfer medium 100 for a testing device are separated from the support 101 by heat during transfer is described. The present invention is not limited to this embodiment. For example, the protective layer 106 and solid-phase reagent layer 103 or the protective layer 106 and release and solid-phase reagent layer 105 may be separated from the support 101 by light. In this case, the release layer 102 or the release and solid-phase reagent layer 105 may contain a light absorber such as carbon black and may make the light absorber absorb light and generate heat, so that the release layer 102 or the release and solid-phase reagent layer 105 is fused to release the solid-phase reagent layer 103 or the release and solid-phase reagent layer 105. Alternatively, the release layer 102 or the release and solid-phase reagent layer 105 may contain a material that changes properties in response to light irradiation and may make the material absorb light, so that the release layer 102 is made fragile to release the protective layer 106 and solid-phase reagent layer 103 or the protective layer 106 and release and solid-phase reagent layer 105.

Examples of a transfer method other than the thermal transfer include a method of pasting a sheet formed of the protective layer 106 and solid-phase reagent layer 103 or formed of the protective layer 106 and release and solid-phase reagent layer 105 over the flow path member 12 by, for example, a tape.

In the embodiment described above, an example in which the flow path is formed throughout the flow path member 12 is described. The present invention is not limited to this embodiment. Examples of the method for forming a flow path in a partial region of the flow path member 12 include a method of forming a flow path wall defining an external edge of the flow path by filling the voids of the flow path member 12 with a hydrophobic material by a known method.

In the embodiment described above, an example in which the resin layers 15 are provided at a plurality of positions on the flow path member 12 is described. However, depending on the kind of the reagent, the resin layer 15 may be provided at one position on the flow path member 12. For example, a testing device capable of detecting a plurality of components at the same time can be obtained when the flow path member 12 that is provided with a resin layer **15*a*1 over which a reagent specifically bindable with a component A contained in the testing liquid 30 is formed as a solid phase and resin layers 15*b*1 and 15*c*1 over which reagents for capturing these reagent and component are formed as solid phases is further provided with a resin layer 15*a*2 over which a reagent specifically bindable with a component B contained in the testing liquid is formed as a solid phase and resin layers 15*b*2 and 15*c*2** over which reagents for capturing these reagent and component are formed as solid phases.

In the embodiment described above, an example in which the testing liquid 30 is hydrophilic is described. However, the testing liquid is not limited to a hydrophilic liquid. For example, the testing liquid may be a solvophilic liquid containing an organic solvent such as alcohols such as methyl alcohol, ethyl alcohol, 1-propyl alcohol, and 2-propyl alcohol, and ketones such as acetone and methyl ethyl ketone (MEK). In this case, the term “hydrophilic” in the embodiment described above is replaced by “hydrophobic”, and the term “hydrophobic” is replaced by “hydrophilic”.

EXAMPLES

The present invention will be described by way of Examples. The present invention should not be construed as being limited to these Examples.

Preparation Example 1

—Preparation of Back Layer Coating Liquid—

A silicone-based rubber emulsion (available from Shin-Etsu Chemical Co., Ltd., KS779H with a solid concentration of 30% by mass) (16.8 parts by mass), a chloroplatinic acid catalyst (0.2 parts by mass), and toluene (83 parts by mass) were mixed, to obtain a back layer coating liquid.

Preparation Example 2

—Preparation of Release and Solid-Phase Reagent Layer (for Immobilization) Coating Liquid—

A coating liquid (available from Ricoh Co., Ltd., B110AX stripping solution) containing carnauba wax (90 parts by mass), an ethylene-vinyl acetate copolymer (1 part by mass), a styrene-butadiene copolymer (4 parts by mass), a butadiene rubber (4 parts by mass), an acrylonitrile-butadiene copolymer (1 part by mass), and a toluene/methyl ethyl ketone (at a ratio by volume of 7/3) solvent was used as a release and solid-phase reagent layer (for immobilization) coating liquid.

Preparation Example 3

—Preparation of Solid-Phase Reagent Layer (for Release) Coating Liquid—

A polyvinyl butyral resin (available from Sekisui Chemical Co., Ltd., BL-1 with a butyralization degree of 64 mol %) (5 parts by mass) and ethanol (95 parts by mass) were mixed, to prepare a solid-phase reagent layer (for release) coating liquid of Preparation example 3.

Preparation Example 4

—Preparation of Test Line Reagent Coating Liquid—

As an antibody diluting fluid, a Dulbecco’s phosphate buffered saline (free of Ca and Mg, D-PBS (−) available from Nacalai Tesque, Inc., 14249-95) was added to an anti-human IgG antibody (available from Sigma-Aldrich Co., LLC., 11886) to be 100 μg/mL, to prepare a test line reagent coating liquid of Preparation example 4.

Preparation Example 5

—Preparation of Control Line Reagent Coating Liquid—

As an antibody diluting fluid, D-PBS (−) mentioned above was added to human IgG (available from Sigma-Aldrich Co., LLC., I2511-10MG) to be 100 μg/mL, to prepare a control line reagent coating liquid of Preparation example 5.

Preparation Example 6

—Preparation of Labeled Antibody Reagent Coating Liquid—

A gold colloid-labeled anti-human IgG antibody (available from BAW Inc., Gold, with an average particle diameter of 40 nm and OD=15) was prepared as a labeled antibody reagent coating liquid of Preparation example 6.

Preparation Example 7

—Preparation of Test Line Reagent Coating Liquid—

As an antibody diluting fluid, a Dulbecco’s phosphate buffered saline (free of Ca and Mg, D-PBS (—) available from Nacalai Tesque, Inc., 14249-95) was added to an anti-hCG monoclonal antibody (available from Medix Biochemica Inc., an anti-alpha subunit 6601, SPR-5) to be 100 μg/mL, to prepare a test line reagent coating liquid of Preparation example 7.

Preparation Example 8

—Preparation of Control Line Reagent Coating Liquid—

As an antibody diluting fluid, D-PBS (−) mentioned above was added to an anti-mouse IgG antibody (available from Wako Pure Chemical Industries, Ltd., 566-70621) to be 100 μg/mL, to prepare a control line reagent coating liquid of Preparation example 8.

Preparation Example 9

—Preparation of Labeled Antibody Reagent Coating Liquid—

A $KH_2PO_4$ buffer (with pH of 7.0) prepared to 50 mM (1 mL), and subsequently an anti-hCG monoclonal antibody (available from Medix Biochemica Inc., anti-hCG 5008 SP-5) prepared to 50 μg/mL (1 mL) were added to a gold colloid solution (available from BBI Solutions Inc., EMGC50) (9 mL) and stirred. The resultant was left to stand still for 10 minutes. To the resultant, a 1% by mass polyethylene glycol aqueous solution (available from Wako Pure Chemical Industries, Ltd., 168-11285) (550 μL) was added and stirred, and then a 10% by mass BSA aqueous solution (available from Sigma-Aldrich Co., LLC., A-7906) (1.1 mL) was added and stirred.

Subsequently, this solution was centrifuged for 30 minutes. The supernatant was removed from this solution in a manner that the solution would remain by about 1 mL. The remaining solution was subjected to gold colloid re-dispersion with an ultrasonic cleaning machine. The centrifugation was performed with a centrifuge (available from Hitachi Koki Co., Ltd., HIMAC CF16RN) at a centrifugal acceleration of 8,000×g at 4 degrees C. Subsequently, the solution was dispersed in a gold colloid preservative solution (20 mM Tris-HCl buffer (with pH of 8.2), 0.05% by mass polyethylene glycol, 150 mM NaCl, a 1% by mass BSA aqueous solution, and a 0.1% by mass $NaN_3$ aqueous solution) (20 mL) and again centrifuged under the same conditions as described above. Subsequently, the supernatant was removed in a manner that the resultant solution would remain by about 1 mL. The remaining solution was subjected to gold colloid re-dispersion with an ultrasonic cleaning machine. These operations were repeated to obtain OD=15 in the gold colloid preservative solution, to obtain a labeled antibody reagent coating liquid or Preparation example 9.

Preparation Example 10

—Preparation of Release and Solid-Phase Reagent Layer (for Immobilization) Coating Liquid—

A polyethylene wax (available from Toyo ADL Corporation, POLYWAX 1000, with a melting point of 99 degrees C. and a penetration of 2 at 25 degrees C.) (14 parts by mass), an ethylene-vinyl acetate copolymer (available from Du Pont-Mitsui Polychemicals Co., Ltd., EV-150, with a weight average molecular weight of 2,100 and VAc of 21%) (6 parts by mass), toluene (60 parts by mass), and methyl ethyl ketone (20 parts by mass) were subjected to dispersion until the average particle diameter became 2.5 μm, to obtain a release and solid-phase reagent layer (for immobilization) coating liquid of Preparation example 10.

Example 1

<Production of Thermal Transfer Medium for Test Line>

—Formation of Back Layer—

The back layer coating liquid of Preparation example 1 was coated over one surface of a support, which was a polyethylene terephthalate (PET) film having an average thickness of 4.5 μm (available from Toray Industries, Inc., LUMIRROR F57), and dried at 80 degrees C. for 10 seconds, to form a back layer having an average thickness of 0.02 μm.

—Formation of Release and Solid-Phase Reagent Layer (for Immobilization)—

Next, the release and solid-phase reagent layer (for immobilization) coating liquid of Preparation example 2 was coated over a surface of the PET film opposite to the surface over which the back layer was formed, and dried at 40 degrees C. for 10 seconds, to form a release layer having an average thickness of 20 μm.

—Production of Thermal Transfer Medium for Test Line—

Subsequently, the test line reagent coating liquid of Preparation example 4 was coated over the release and solid-phase reagent layer (for immobilization) by 12 μL per unit area ($cm^2$) to form a water film. Subsequently, the thermal transfer medium was set in a container maintained at a relative humidity of 80% so as not for the water film to dry, and left to stand still at 25 degrees C. for 10 minutes. After standing still, the thermal transfer medium was peeled from the water film, and surface of the release and solid-phase reagent layer was cleaned under the conditions described below.

—Cleaning—

The thermal transfer medium peeled from the water film was pasted over a shaker (SHAKE-XR mounted with WR-3636, both available from Taitec Corporation), in a manner that the surface over which the reagent was to be formed as a solid phase faced outside.

Subsequently, distilled water was poured onto the surface over which the reagent was to be formed as a solid phase by 100 μL per unit area ($cm^2$) of the surface, and then the thermal transfer medium was gently shaken at 25 degrees C. at a shaking speed of 20 r/min for 1 minute. After shaking was completed, the supernatant liquid after cleaning was removed. This operation was repeated a total of 5 times. Finally, the supernatant after cleaning was sufficiently drained off from the surface of the thermal transfer medium, for cleaning to be completed. After cleaning, the thermal transfer medium was dried in a dessicator of a temperature of 25 degrees C. and a relative humidity of 20% for 15 minutes, to form the reagent as a solid phase over the release and solid-phase reagent layer (for immobilization).

Subsequently, a protective layer coating liquid 1 produced by dissolving trehalose (special grade D(+)-trehalose dihydrate, available from Kishida Chemical Co., Ltd.) in purified water to be 1% by mass was coated over the surface of the release and solid-phase reagent layer (for immobilization) by 100 μl per unit area ($cm^2$) and subjected to vacuum drying with a vacuum dryer (available from As One Corporation, AVO-200NB-CR) for 60 minutes, to form a protective layer having an average thickness of 10 μm in a manner to cover the reagent over the surface of the release and solid-phase reagent layer (for immobilization). In this way, the thermal transfer medium for a test line of Example 1 was obtained.

The average thickness of the protective layer was calculated by multiplying the amount of the protective layer coating liquid added per area by the concentration of the protective layer coating liquid.

<Production of Thermal Transfer Medium for Control Line>

A thermal transfer medium for a control line of Example 1 was obtained in the same manner as in the production of the thermal transfer medium for a test line, except that the test line reagent coating liquid of Preparation example 4 used in the production of the thermal transfer medium for a test line was changed to the control line reagent coating liquid of Preparation example 5.

<Production of Thermal Transfer Medium for Labeled Antibody>

In the same manner as in the production of the thermal transfer medium for a test line, a back layer and a release and solid-phase reagent layer (for immobilization) were formed over one surface of a support, which was a polyethylene terephthalate (PET) film having an average thickness of 4.5 μm (available from Toray Industries, Inc., LUMIRROR F57). Subsequently, the solid-phase reagent layer (for release) coating liquid of Preparation example 3 was coated over the release and solid-phase reagent layer (for immobilization) and dried at 40 degrees C. for 10 minutes, to form a solid-phase reagent layer (for release) having an average thickness of 5 μm.

Subsequently, the labeled antibody reagent coating liquid of Preparation example 6 was coated over the solid-phase reagent layer (for release) by 14 $\mu L/cm^2$ and dried in a vacuum dryer at 25 degrees C. for 5 hours, to form the reagent as a solid phase over the solid-phase reagent layer (for release). In this way, the thermal transfer medium for a labeled antibody of Example 1 was obtained.

<Production of Testing Device>

Figure 10A:
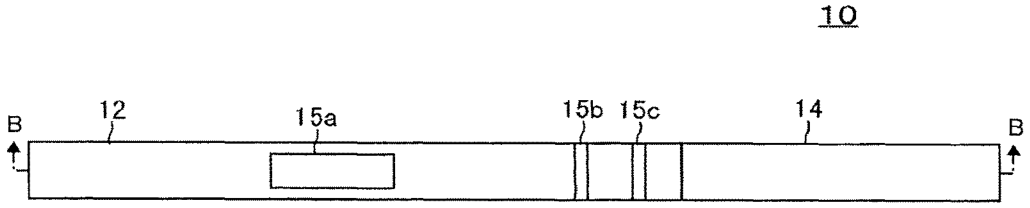
FIG. 10A is a top view of an example of a testing device used in Examples.
Figure 10B:
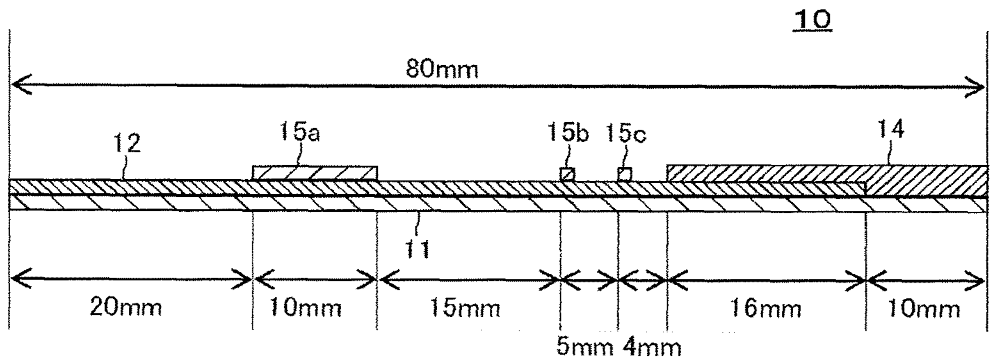
FIG. 10B is a cross-sectional view taken along a line B-B of FIG. 10A.

In the manner described below, a testing device illustrated in FIG. 10A and FIG. 10B was produced. FIG. 10A is a top view of the testing device of Example. FIG. 10B is a cross-sectional view of the testing device of FIG. 10A taken along a line B-B.

Note that the testing device was produced on the same day as the thermal transfer medium for a test line, the thermal transfer medium for a control line, and the thermal transfer medium for a labeled antibody were produced.

—Production of Paper Substrate—

As a thermoplastic resin, a polyester-based hot-melt adhesive (available from Toagosei Co., Ltd., ARONMELT PES375S40) was heated to 190 degrees C., and then with a roll coater, coated over a PET film (available from Toray Industries, Inc., LUMIRROR S10, with an average thickness of 50 μm) 11 cut into a size of 40 mm in width and 80 mm in length to have a thickness of 50 μm over the PET film, to form an adhesive layer.

The PET film 11 over which the adhesive layer was formed was left to stand still for 2 hours or longer. Subsequently, a nitrocellulose membrane (available from Merck Millipore Corporation, HF180, with a voidage of 70%) cut into a size of 40 mm in width and 70 mm in length was overlapped over the adhesive layer-coated surface in a manner that one end of the adhesive layer-coated surface in the longer direction and one end of each member in the longer direction (this end is referred to as upstream end, and the opposite end is referred to as downstream end) would coincide with each other, and a load of 1 $kgf/cm^2$ was applied to the overlapped members at a temperature of 150 degrees C. for 10 seconds. Finally, the obtained product was cut along the longer direction into a size of 4 mm in width and 80 mm in length, to obtain a paper substrate 12. The voidage of the paper substrate 12 was calculated according to a calculation formula 1 below based on the basis weight ($g/m^2$) of the paper substrate, the thickness (μm) of the paper substrate, and specific gravity of the component of the paper substrate. As a result, the voidage of the paper substrate was 70%. A paper substrate having a voidage of 40% or higher but 90% or lower can be said to be a porous paper substrate.

$$\text{Voidage (\%)}=\{1-[\text{basis weight } (g/m^2)/\text{thickness } (\mu m)/\text{specific gravity of the component}]\}\times 100 \quad \text{[Calculation formula 1]}$$

—Transfer of Labeled Antibody—

The paper substrate 12 and the thermal transfer medium for a labeled antibody was overlapped with each other in a manner that the surface of the thermal transfer medium having the reagent formed as a solid phase faced the paper substrate 12. Subsequently, with a thermal transfer printer, the thermal transfer medium for a labeled antibody was transferred in a pattern of 3 mm in width and 10 mm in length (resin layer 15*a*) onto the paper substrate 12 at a position away from the upstream end by 20 mm, as illustrated in FIG. 10A and FIG. 10B.

The thermal transfer printer was equipped with a thermal head having a dot density of 300 dpi (available from TDK Corporation), and constructed as an evaluation system having a printing speed of 8.7 mm/sec and an applied energy of 0.35 mJ/dot.

—Transfer of Test Line and Control Line—

As illustrated in FIG. 10A and FIG. 10B, the thermal transfer medium for a test line was transferred in a line shape of 4 mm in height and 1 mm in length (test line 15*b*) onto a position away from the position to which the thermal transfer medium for a labeled antibody was transferred by 15 mm. Then, the thermal transfer medium for a control line was transferred in a line shape of 4 mm in height and 1 mm in length (control line 15*c*) onto a position away from the position to which the thermal transfer medium for a test line was transferred by 5 mm. The lines were formed under the same printing conditions as used for transferring the labeled antibody.

—Production of Absorbing Member—

An absorbing member 14 (available from Merck Millipore Corporation, SUREWICK C248) was provided as illustrated in FIG. 10A and FIG. 10B, to obtain an immunochromatoassay (testing device 10) of Example 1.

<Evaluation of Line>

—Preparation of Testing Liquid—

As a developing liquid, a D-PBS (+) solution of 0.1% by mass TWEEN 20 (available from Sigma-Aldrich Co., LLC., P9416-50ML) was prepared.

Subsequently, the developing liquid was added to human IgG to be prepared to 500 μg/mL, to obtain a testing liquid.

—Reaction—

The testing liquid (100 μL) was dropped onto the upstream end of the immunochromatoassay illustrated in FIG. 10A and FIG. 10B. Fifteen minutes later, line visibility and a test line density were measured. The results are presented in Table 3-1.

—Evaluation of Line Visibility—

The test line on the immunochromatoassay in which the reaction was completed was visually observed to evaluate visibility according to the criteria described below. The result is presented in Table 3-1.

[Evaluation Criteria]

A: A color was developed on the line uniformly densely entirely, without unevenness in the color developing density in the width direction.

B: A color was developed on the line.

C: A color was developed on the line, but considerably palely.

—Measurement of Line Density Using Thermal Transfer Medium for Test Line Immediately after Produced—

The immunochromatoassay in which the reaction was completed was stored in a housing case for measurement, and the color developing density on the test line was obtained from a reading measured with a chromatoreader (available from Otsuka Electronics Co., Ltd., DIASCAN 10) as a "reading immediately after production". The value is presented in Table 3-1. A greater reading is more preferable, because the color development on the test line was denser.

—Measurement of Line Density Using Thermal Transfer Medium for Test Line after Sliding—

Two pieces each having 1 cm per side were cut out from a produced thermal transfer medium for a test line, and overlapped with each other. The 2 pieces were overlapped in a manner that the first thermal transfer medium for a test line was put to have the protective layer side below and the back layer side above and the second thermal transfer medium for a test line was overlapped over the first one in the same manner. The overlapped surfaces were the back layer of the first one and the protective layer of the second one. Drawing paper (with 5 cm per side and a thickness of 200 μm) was put over the overlapped 2 thermal transfer media for a test line, a weight plate of 1 kg was put over the drawing paper from above, and the thermal transfer media were left to stand for 10 minutes in this state. Subsequently, the 2 thermal transfer media for a test line each having 1 cm per side were taken out. The second thermal transfer medium for a test line having the protective layer overlapped over the back layer was used to produce an immunochromato kit in the same manner as in Example 1 and measure a test line in the same manner as in the line density measurement described above to obtain a color developing density on the test line from a reading as a "reading after sliding". The value is presented in Table 3-1.

—Measurement of Line Density Using Thermal Transfer Medium for Test Line 5 Days after Production—

A thermal transfer medium for a test line 5 days after production (left to stand in an environment with a temperature of 25 degrees C. and a relative humidity of 45%) was used to produce a testing device and measure a line density according to the same operation as described above. The result is presented in Table 3-1 as a "reading 5 days after production".

—Evaluation of Temporal Stability—

A degree of degradation was calculated according to a mathematical formula 1 described below to evaluate temporal stability according to the criterial described below. The result is presented in Table 3-1.

Degree of degradation (%)=[|("reading immediately after production"−"reading 5 days after production")|/"reading immediately after production"]×100 <Mathematical formula 1>

Note that || in the mathematical formula 1 indicates an absolute value.

[Evaluation Criteria]

A: The degree of degradation is less than 20%.

B: The degree of degradation is 20% or greater.

Example 2

An immunochromatoassay (testing device 10) of Example 2 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-1.

<Production of Thermal Transfer Medium for Test Line>

A thermal transfer medium for a test line of Example 2 was obtained in the same manner as in Example 1, except that unlike in the production of the thermal transfer medium for a test line of Example 1, a protective layer coating liquid 2 produced by dissolving trehalose (special grade D(+)-trehalose dihydrate, available from Kishida Chemical Co., Ltd.) in purified water to be 0.05% by mass was used to form a protective layer having an average thickness of 0.5 μm in a manner to cover the reagent over the surface of the release and solid-phase reagent layer (for immobilization).

<Production of Thermal Transfer Medium for Control Line>

A thermal transfer medium for a control line of Example 2 was obtained in the same manner as in the production of the thermal transfer medium for a test line of Example 1, except that the protective layer coating liquid 1 used in the production of the thermal transfer medium for a test line of Example 1 was changed to the protective layer coating liquid 2 prepared in the production of the thermal transfer medium for a test line of Example 2.

Example 3

An immunochromatoassay (testing device 10) of Example 3 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-1.

<Production of Thermal Transfer Medium for Test Line>

A thermal transfer medium for a test line of Example 3 was obtained in the same manner as in Example 1, except that unlike in the production of the thermal transfer medium for a test line of Example 1, a protective layer coating liquid 3 produced by dissolving trehalose (special grade D(+)-trehalose dihydrate, available from Kishida Chemical Co., Ltd.) in purified water to be 3% by mass was used to form a protective layer having an average thickness of 30 μm in a manner to cover the reagent over the surface of the release and solid-phase reagent layer (for immobilization).

<Production of Thermal Transfer Medium for Control Line>

A thermal transfer medium for a control line of Example 3 was obtained in the same manner as in the production of the thermal transfer medium for a test line of Example 1, except that the protective layer coating liquid 1 used in the production of the thermal transfer medium for a test line of Example 1 was changed to the protective layer coating liquid 3 prepared in the production of the thermal transfer medium for a test line of Example 3.

Example 4

An immunochromatoassay (testing device 10) of Example 4 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-1.

<Production of Thermal Transfer Medium for Test Line>

A thermal transfer medium for a test line of Example 4 was obtained in the same manner as in Example 1, except that unlike in the production of the thermal transfer medium for a test line of Example 1, a protective layer coating liquid 4 produced by dissolving inositol (available from Shikishima Starch Mfg. Co., Ltd.) in purified water to be 0.05% by mass was used to form a protective layer having an average thickness of 0.5 μm in a manner to cover the reagent over the surface of the release and solid-phase reagent layer (for immobilization).

<Production of Thermal Transfer Medium for Control Line>

A thermal transfer medium for a control line of Example 4 was obtained in the same manner as in the production of the thermal transfer medium for a test line of Example 1, except that the protective layer coating liquid 1 used in the production of the thermal transfer medium for a test line of Example 1 was changed to the protective layer coating liquid 4 prepared in the production of the thermal transfer medium for a test line of Example 4.

Example 5

An immunochromatoassay (testing device 10) of Example 5 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-1.

<Production of Thermal Transfer Medium for Test Line>

A thermal transfer medium for a test line of Example 5 was obtained in the same manner as in Example 1, except that unlike in the production of the thermal transfer medium for a test line of Example 1, a protective layer coating liquid 5 produced by dissolving inositol (available from Shikishima Starch Mfg. Co., Ltd.) in purified water to be 3% by mass was used to form a protective layer having an average thickness of 30 μm in a manner to cover the reagent over the surface of the release and solid-phase reagent layer (for immobilization).

<Production of Thermal Transfer Medium for Control Line>

A thermal transfer medium for a control line of Example 5 was obtained in the same manner as in the production of the thermal transfer medium for a test line of Example 1, except that the protective layer coating liquid 1 used in the production of the thermal transfer medium for a test line of Example 1 was changed to the protective layer coating liquid 5 prepared in the production of the thermal transfer medium for a test line of Example 5.

Example 6

An immunochromatoassay (testing device 10) of Example 6 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-1.

<Production of Thermal Transfer Medium for Test Line>

A thermal transfer medium for a test line of Example 6 was obtained in the same manner as in Example 1, except that unlike in the production of the thermal transfer medium for a test line of Example 1, a protective layer coating liquid 6 produced by dissolving glucose (D(+)-glucose available from Wako Pure Chemical Industries, Ltd.) in purified water to be 0.05% by mass was used to form a protective layer having an average thickness of 0.5 μm in a manner to cover the reagent over the surface of the release and solid-phase reagent layer (for immobilization).

<Production of Thermal Transfer Medium for Control Line>

A thermal transfer medium for a control line of Example 6 was obtained in the same manner as in the production of the thermal transfer medium for a test line of Example 1, except that the protective layer coating liquid 1 used in the production of the thermal transfer medium for a test line of Example 1 was changed to the protective layer coating liquid 6 prepared in the production of the thermal transfer medium for a test line of Example 6.

Example 7

An immunochromatoassay (testing device 10) of Example 7 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-1.

<Production of Thermal Transfer Medium for Test Line>

A thermal transfer medium for a test line of Example 7 was obtained in the same manner as in Example 1, except that unlike in the production of the thermal transfer medium for a test line of Example 1, a protective layer coating liquid 7 produced by dissolving glucose (D(+)-glucose available from Wako Pure Chemical Industries, Ltd.) in purified water to be 3% by mass was used to form a protective layer having an average thickness of 30 μm in a manner to cover the reagent over the surface of the release and solid-phase reagent layer (for immobilization).

<Production of Thermal Transfer Medium for Control Line>

A thermal transfer medium for a control line of Example 7 was obtained in the same manner as in the production of the thermal transfer medium for a test line of Example 1, except that the protective layer coating liquid 1 used in the production of the thermal transfer medium for a test line of Example 1 was changed to the protective layer coating liquid 7 prepared in the production of the thermal transfer medium for a test line of Example 7.

Example 8

An immunochromatoassay (testing device 10) of Example 8 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-1.

<Production of Thermal Transfer Medium for Test Line>

A thermal transfer medium for a test line of Example 8 was obtained in the same manner as in Example 1, except that unlike in the production of the thermal transfer medium for a test line of Example 1, a protective layer coating liquid 8 produced by dissolving fructose (D(−)-fructose available from Wako Pure Chemical Industries, Ltd.) in purified water to be 0.05% by mass was used to form a protective layer having an average thickness of 0.5 μm in a manner to cover the reagent over the surface of the release and solid-phase reagent layer (for immobilization).

<Production of Thermal Transfer Medium for Control Line>

A thermal transfer medium for a control line of Example 8 was obtained in the same manner as in the production of the thermal transfer medium for a test line of Example 1, except that the protective layer coating liquid 1 used in the production of the thermal transfer medium for a test line of Example 1 was changed to the protective layer coating liquid 8 prepared in the production of the thermal transfer medium for a test line of Example 8.

Example 9

An immunochromatoassay (testing device 10) of Example 9 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-1.

<Production of Thermal Transfer Medium for Test Line>

A thermal transfer medium for a test line of Example 9 was obtained in the same manner as in Example 1, except that unlike in the production of the thermal transfer medium for a test line of Example 1, a protective layer coating liquid 9 produced by dissolving fructose (D(−)-fructose available from Wako Pure Chemical Industries, Ltd.) in purified water to be 3% by mass was used to form a protective layer having an average thickness of 30 μm in a manner to cover the reagent over the surface of the release and solid-phase reagent layer (for immobilization).

<Production of Thermal Transfer Medium for Control Line>

A thermal transfer medium for a control line of Example 9 was obtained in the same manner as in the production of the thermal transfer medium for a test line of Example 1, except that the protective layer coating liquid 1 used in the production of the thermal transfer medium for a test line of Example 1 was changed to the protective layer coating liquid 9 prepared in the production of the thermal transfer medium for a test line of Example 9.

Example 10

An immunochromatoassay (testing device 10) of Example 10 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-1.

<Production of Thermal Transfer Medium for Test Line>

A thermal transfer medium for a test line of Example 10 was obtained in the same manner as in Example 1, except that unlike in the production of the thermal transfer medium for a test line of Example 1, a protective layer coating liquid 10 produced by dissolving galactose (D(+)-galactose available from Wako Pure Chemical Industries, Ltd.) in purified water to be 0.05% by mass was used to form a protective layer having an average thickness of 0.5 μm in a manner to cover the reagent over the surface of the release and solid-phase reagent layer (for immobilization).

<Production of Thermal Transfer Medium for Control Line>

A thermal transfer medium for a control line of Example 10 was obtained in the same manner as in the production of the thermal transfer medium for a test line of Example 1, except that the protective layer coating liquid 1 used in the production of the thermal transfer medium for a test line of Example 1 was changed to the protective layer coating liquid 10 prepared in the production of the thermal transfer medium for a test line of Example 10.

Example 11

An immunochromatoassay (testing device 10) of Example 11 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-1.

<Production of Thermal Transfer Medium for Test Line>

A thermal transfer medium for a test line of Example 11 was obtained in the same manner as in Example 1, except that unlike in the production of the thermal transfer medium for a test line of Example 1, a protective layer coating liquid 11 produced by dissolving galactose (D(+)-galactose available from Wako Pure Chemical Industries, Ltd.) in purified water to be 3% by mass was used to form a protective layer having an average thickness of 30 μm in a manner to cover the reagent over the surface of the release and solid-phase reagent layer (for immobilization).

<Production of Thermal Transfer Medium for Control Line>

A thermal transfer medium for a control line of Example 11 was obtained in the same manner as in the production of the thermal transfer medium for a test line of Example 1, except that the protective layer coating liquid 1 used in the production of the thermal transfer medium for a test line of Example 1 was changed to the protective layer coating liquid 11 prepared in the production of the thermal transfer medium for a test line of Example 11.

Example 12

An immunochromatoassay (testing device 10) of Example 12 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-1.

<Production of Thermal Transfer Medium for Test Line>

A thermal transfer medium for a test line of Example 12 was obtained in the same manner as in Example 1, except that unlike in the production of the thermal transfer medium for a test line of Example 1, a protective layer coating liquid 12 produced by dissolving sucrose (available from Wako Pure Chemical Industries, Ltd.) in purified water to be 0.05% by mass was used to form a protective layer having an average thickness of 0.5 μm in a manner to cover the reagent over the surface of the release and solid-phase reagent layer (for immobilization).

<Production of Thermal Transfer Medium for Control Line>

A thermal transfer medium for a control line of Example 12 was obtained in the same manner as in the production of the thermal transfer medium for a test line of Example 1, except that the protective layer coating liquid 1 used in the production of the thermal transfer medium for a test line of Example 1 was changed to the protective layer coating liquid 12 prepared in the production of the thermal transfer medium for a test line of Example 12.

Example 13

An immunochromatoassay (testing device 10) of Example 13 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-1.

<Production of Thermal Transfer Medium for Test Line>

A thermal transfer medium for a test line of Example 13 was obtained in the same manner as in Example 1, except that unlike in the production of the thermal transfer medium for a test line of Example 1, a protective layer coating liquid 13 produced by dissolving sucrose (available from Wako Pure Chemical Industries, Ltd.) in purified water to be 3% by mass was used to form a protective layer having an average thickness of 30 μm in a manner to cover the reagent over the surface of the release and solid-phase reagent layer (for immobilization).

<Production of Thermal Transfer Medium for Control Line>

A thermal transfer medium for a control line of Example 13 was obtained in the same manner as in the production of the thermal transfer medium for a test line of Example 1, except that the protective layer coating liquid 1 used in the production of the thermal transfer medium for a test line of Example 1 was changed to the protective layer coating liquid 13 prepared in the production of the thermal transfer medium for a test line of Example 13.

Example 14

An immunochromatoassay (testing device 10) of Example 14 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-1.

<Production of Thermal Transfer Medium for Test Line>

A thermal transfer medium for a test line of Example 14 was obtained in the same manner as in Example 1, except that unlike in the production of the thermal transfer medium for a test line of Example 1, a protective layer coating liquid 14 produced by dissolving lactose (lactose monohydrate available from Wako Pure Chemical Industries, Ltd.) in purified water to be 0.05% by mass was used to form a protective layer having an average thickness of 0.5 μm in a manner to cover the reagent over the surface of the release and solid-phase reagent layer (for immobilization).

<Production of Thermal Transfer Medium for Control Line>

A thermal transfer medium for a control line of Example 14 was obtained in the same manner as in the production of the thermal transfer medium for a test line of Example 1, except that the protective layer coating liquid 1 used in the production of the thermal transfer medium for a test line of Example 1 was changed to the protective layer coating liquid 14 prepared in the production of the thermal transfer medium for a test line of Example 14.

Example 15

An immunochromatoassay (testing device 10) of Example 15 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-1.

<Production of Thermal Transfer Medium for Test Line>

A thermal transfer medium for a test line of Example 15 was obtained in the same manner as in Example 1, except that unlike in the production of the thermal transfer medium for a test line of Example 1, a protective layer coating liquid 15 produced by dissolving lactose (lactose monohydrate available from Wako Pure Chemical Industries, Ltd.) in purified water to be 3% by mass was used to form a protective layer having an average thickness of 30 μm in a manner to cover the reagent over the surface of the release and solid-phase reagent layer (for immobilization).

<Production of Thermal Transfer Medium for Control Line>

A thermal transfer medium for a control line of Example 15 was obtained in the same manner as in the production of the thermal transfer medium for a test line of Example 1, except that the protective layer coating liquid 1 used in the production of the thermal transfer medium for a test line of Example 1 was changed to the protective layer coating liquid 15 prepared in the production of the thermal transfer medium for a test line of Example 15.

Example 16

An immunochromatoassay (testing device 10) of Example 16 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-1.

<Production of Thermal Transfer Medium for Test Line>

A thermal transfer medium for a test line of Example 16 was obtained in the same manner as in Example 1, except that unlike in the production of the thermal transfer medium for a test line of Example 1, a protective layer coating liquid 16 produced by dissolving maltose (D(+)-maltose monohydrate available from Wako Pure Chemical Industries, Ltd.) in purified water to be 0.05% by mass was used to form a protective layer having an average thickness of 0.5 μm in a manner to cover the reagent over the surface of the release and solid-phase reagent layer (for immobilization).

<Production of Thermal Transfer Medium for Control Line>

A thermal transfer medium for a control line of Example 16 was obtained in the same manner as in the production of the thermal transfer medium for a test line of Example 1, except that the protective layer coating liquid 1 used in the production of the thermal transfer medium for a test line of Example 1 was changed to the protective layer coating liquid 16 prepared in the production of the thermal transfer medium for a test line of Example 16.

Example 17

An immunochromatoassay (testing device 10) of Example 17 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-1.

<Production of Thermal Transfer Medium for Test Line>

A thermal transfer medium for a test line of Example 17 was obtained in the same manner as in Example 1, except that unlike in the production of the thermal transfer medium for a test line of Example 1, a protective layer coating liquid 17 produced by dissolving maltose (D(+)-maltose monohydrate available from Wako Pure Chemical Industries, Ltd.) in purified water to be 3% by mass was used to form a protective layer having an average thickness of 30 μm in a manner to cover the reagent over the surface of the release and solid-phase reagent layer (for immobilization).

<Production of Thermal Transfer Medium for Control Line>

A thermal transfer medium for a control line of Example 17 was obtained in the same manner as in the production of the thermal transfer medium for a test line of Example 1, except that the protective layer coating liquid 1 used in the production of the thermal transfer medium for a test line of Example 1 was changed to the protective layer coating liquid 17 prepared in the production of the thermal transfer medium for a test line of Example 17.

Example 18

An immunochromatoassay (testing device 10) of Example 18 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-1.

<Production of Thermal Transfer Medium for Test Line>

A thermal transfer medium for a test line of Example 18 was obtained in the same manner as in Example 1, except that unlike in the production of the thermal transfer medium for a test line of Example 1, a protective layer coating liquid 18 produced by dissolving cellobiose (D(+)-cellobiose available from Nacalai Tesque, Inc.) in purified water to be 0.05% by mass was used to form a protective layer having an average thickness of 0.5 μm in a manner to cover the reagent over the surface of the release and solid-phase reagent layer (for immobilization).

<Production of Thermal Transfer Medium for Control Line>

A thermal transfer medium for a control line of Example 18 was obtained in the same manner as in the production of the thermal transfer medium for a test line of Example 1, except that the protective layer coating liquid 1 used in the production of the thermal transfer medium for a test line of Example 1 was changed to the protective layer coating liquid 18 prepared in the production of the thermal transfer medium for a test line of Example 18.

Example 19

An immunochromatoassay (testing device 10) of Example 19 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-1.

<Production of Thermal Transfer Medium for Test Line>

A thermal transfer medium for a test line of Example 19 was obtained in the same manner as in Example 1, except that unlike in the production of the thermal transfer medium for a test line of Example 1, a protective layer coating liquid 19 produced by dissolving cellobiose (D(+)-cellobiose available from Nacalai Tesque, Inc.) in purified water to be 3% by mass was used to form a protective layer having an average thickness of 30 μm in a manner to cover the reagent over the surface of the release and solid-phase reagent layer (for immobilization).

<Production of Thermal Transfer Medium for Control Line>

A thermal transfer medium for a control line of Example 19 was obtained in the same manner as in the production of the thermal transfer medium for a test line of Example 1, except that the protective layer coating liquid 1 used in the production of the thermal transfer medium for a test line of Example 1 was changed to the protective layer coating liquid 19 prepared in the production of the thermal transfer medium for a test line of Example 19.

Example 20

An immunochromatoassay (testing device 10) of Example 20 was produced in the same manner as in Example 1, except that unlike in Example 1, the test line reagent coating liquid of Preparation example 4 was changed to the test line reagent coating liquid of Preparation example 7, the control line reagent coating liquid of Preparation example 5 was changed to the control line reagent coating liquid of Preparation example 8, and the labeled antibody reagent coating liquid of Preparation example 6 was changed to the labeled antibody reagent coating liquid of Preparation example 9. The immunochromatoassay was evaluated in the same manner as in Example 1. The results are presented in Table 3-1.

Example 21

An immunochromatoassay (testing device 10) of Example 21 was produced in the same manner as in Example 1, except that unlike in Example 1, the nitrocellulose membrane pasted over the adhesive layer of the paper substrate was changed to hydrophilic polytetrafluoroethylene (PTFE) [JMWP14225 available from Merck Millipore Corporation, with a voidage of 80%]. The immunochromatoassay was evaluated in the same manner as in Example 1. The results are presented in Table 3-1.

Example 22

An immunochromatoassay (testing device 10) of Example 22 was produced in the same manner as in Example 1, except that unlike in Example 1, the release and solid-phase reagent layer (for immobilization) coating liquid of Preparation example 2 was changed to the release and solid-phase reagent layer (for immobilization) coating liquid of Preparation example 10. The immunochromatoassay was evaluated in the same manner as in Example 1. The results are presented in Table 3-1.

Comparative Example 1

An immunochromatoassay (testing device 10) of Comparative Example 1 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-2.

<Production of Thermal Transfer Medium for Test Line>

Unlike in the production of the thermal transfer medium for a test line of Example 1, after the release and solid-phase reagent layer (for immobilization) was coated with the test line reagent coating liquid by 12 μL per unit area ($cm^2$) to form a water film and cleaned, the thermal transfer medium was dried in a dessicator having a relative humidity of 20% without being coated with the protective layer coating liquid 1, to form the reagent as a solid phase over the release and solid-phase reagent layer (for immobilization). In this way, the thermal transfer medium for a test line of Comparative Example 1 was obtained.

<Production of Thermal Transfer Medium for Control Line>

A thermal transfer medium for a control line of Comparative Example 1 was obtained in the same manner as in the production of the thermal transfer medium for a test line, except unlike in the production of the thermal transfer medium for a test line of Example 1, the protective layer coating liquid 1 was not coated.

Comparative Example 2

An immunochromatoassay (testing device 10) of Comparative Example 2 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-2.

<Production of Thermal Transfer Medium for Test Line>

A thermal transfer medium for a test line of Comparative Example 2 was obtained in the same manner as in Example 1, except that unlike in the production of the thermal transfer medium for a test line of Example 1, a protective layer coating liquid 20 produced by dissolving trehalose (special grade D(+)-trehalose dihydrate, available from Kishida Chemical Co., Ltd.) in purified water to be 3.5% by mass was used to form a protective layer having an average thickness of 35 μm in a manner to cover the reagent over the surface of the release and solid-phase reagent layer (for immobilization).

<Production of Thermal Transfer Medium for Control Line>

A thermal transfer medium for a control line of Comparative Example 2 was obtained in the same manner as in the production of the thermal transfer medium for a test line of Example 1, except that the protective layer coating liquid 1 used in the production of the thermal transfer medium for a test line of Example 1 was changed to the protective layer coating liquid 20 prepared in the production of the thermal transfer medium for a test line of Comparative Example 2.

Comparative Example 3

An immunochromatoassay (testing device 10) of Comparative Example 3 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-2.

<Production of Thermal Transfer Medium for Test Line>

A thermal transfer medium for a test line of Comparative Example 3 was obtained in the same manner as in Example 1, except that unlike in the production of the thermal transfer medium for a test line of Example 1, a protective layer coating liquid 21 produced by dissolving trehalose (special grade D(+)-trehalose dihydrate, available from Kishida Chemical Co., Ltd.) in purified water to be 0.03% by mass was used to form a protective layer having an average thickness of 0.3 μm in a manner to cover the reagent over the surface of the release and solid-phase reagent layer (for immobilization).

<Production of Thermal Transfer Medium for Control Line>

A thermal transfer medium for a control line of Comparative Example 3 was obtained in the same manner as in the production of the thermal transfer medium for a test line of Example 1, except that the protective layer coating liquid 1 used in the production of the thermal transfer medium for a test line of Example 1 was changed to the protective layer coating liquid 21 prepared in the production of the thermal transfer medium for a test line of Comparative Example 3.

Comparative Example 4

An immunochromatoassay (testing device 10) of Comparative Example 4 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-2.

<Production of Thermal Transfer Medium for Test Line>

A thermal transfer medium for a test line of Comparative Example 4 was obtained in the same manner as in Example 1, except that unlike in the production of the thermal transfer medium for a test line of Example 1, a protective layer coating liquid 22 produced by dissolving inositol (available from Shikishima Starch Mfg. Co., Ltd.) in purified water to be 3.5% by mass was used to form a protective layer having an average thickness of 35 μm in a manner to cover the reagent over the surface of the release and solid-phase reagent layer (for immobilization).

<Production of Thermal Transfer Medium for Control Line>

A thermal transfer medium for a control line of Comparative Example 4 was obtained in the same manner as in the production of the thermal transfer medium for a test line of Example 1, except that the protective layer coating liquid 1 used in the production of the thermal transfer medium for a test line of Example 1 was changed to the protective layer coating liquid 22 prepared in the production of the thermal transfer medium for a test line of Comparative Example 4.

Comparative Example 5

An immunochromatoassay (testing device 10) of Comparative Example 5 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-2.

<Production of Thermal Transfer Medium for Test Line>

A thermal transfer medium for a test line of Comparative Example 5 was obtained in the same manner as in Example 1, except that unlike in the production of the thermal transfer medium for a test line of Example 1, a protective layer coating liquid 23 produced by dissolving inositol (available from Shikishima Starch Mfg. Co., Ltd.) in purified water to be 0.03% by mass was used to form a protective layer having an average thickness of 0.3 μm in a manner to cover the reagent over the surface of the release and solid-phase reagent layer (for immobilization).

<Production of Thermal Transfer Medium for Control Line>

A thermal transfer medium for a control line of Comparative Example 5 was obtained in the same manner as in the production of the thermal transfer medium for a test line of Example 1, except that the protective layer coating liquid 1 used in the production of the thermal transfer medium for a test line of Example 1 was changed to the protective layer coating liquid 23 prepared in the production of the thermal transfer medium for a test line of Comparative Example 5.

Comparative Example 6

An immunochromatoassay (testing device 10) of Comparative Example 6 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-2.

<Production of Thermal Transfer Medium for Test Line>

A thermal transfer medium for a test line of Comparative Example 6 was obtained in the same manner as in Example 1, except that unlike in the production of the thermal transfer medium for a test line of Example 1, a protective layer coating liquid 24 produced by dissolving glucose (D(+)-glucose available from Wako Pure Chemical Industries, Ltd.) in purified water to be 3.5% by mass was used to form a protective layer having an average thickness of 35 μm in a manner to cover the reagent over the surface of the release and solid-phase reagent layer (for immobilization).

<Production of Thermal Transfer Medium for Control Line>

A thermal transfer medium for a control line of Comparative Example 6 was obtained in the same manner as in the production of the thermal transfer medium for a test line of Example 1, except that the protective layer coating liquid 1 used in the production of the thermal transfer medium for a test line of Example 1 was changed to the protective layer coating liquid 24 prepared in the production of the thermal transfer medium for a test line of Comparative Example 6.

Comparative Example 7

An immunochromatoassay (testing device 10) of Comparative Example 7 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-2.

<Production of Thermal Transfer Medium for Test Line>

A thermal transfer medium for a test line of Comparative Example 7 was obtained in the same manner as in Example 1, except that unlike in the production of the thermal transfer medium for a test line of Example 1, a protective layer coating liquid 25 produced by dissolving glucose (D(+)-glucose available from Wako Pure Chemical Industries, Ltd.) in purified water to be 0.03% by mass was used to form a protective layer having an average thickness of 0.3 μm in a manner to cover the reagent over the surface of the release and solid-phase reagent layer (for immobilization).

<Production of Thermal Transfer Medium for Control Line>

A thermal transfer medium for a control line of Comparative Example 7 was obtained in the same manner as in the production of the thermal transfer medium for a test line of Example 1, except that the protective layer coating liquid 1 used in the production of the thermal transfer medium for a test line of Example 1 was changed to the protective layer coating liquid 25 prepared in the production of the thermal transfer medium for a test line of Comparative Example 7.

Comparative Example 8

An immunochromatoassay (testing device 10) of Comparative Example 8 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-2.

<Production of Thermal Transfer Medium for Test Line>

A thermal transfer medium for a test line of Comparative Example 8 was obtained in the same manner as in Example 1, except that unlike in the production of the thermal transfer medium for a test line of Example 1, a protective layer coating liquid 26 produced by dissolving fructose (D(−)-fructose available from Wako Pure Chemical Industries, Ltd.) in purified water to be 3.5% by mass was used to form a protective layer having an average thickness of 35 μm in a manner to cover the reagent over the surface of the release and solid-phase reagent layer (for immobilization).

<Production of Thermal Transfer Medium for Control Line>

A thermal transfer medium for a control line of Comparative Example 8 was obtained in the same manner as in the production of the thermal transfer medium for a test line of Example 1, except that the protective layer coating liquid 1 used in the production of the thermal transfer medium for a test line of Example 1 was changed to the protective layer coating liquid 26 prepared in the production of the thermal transfer medium for a test line of Comparative Example 8.

Comparative Example 9

An immunochromatoassay (testing device 10) of Comparative Example 9 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-2.

<Production of Thermal Transfer Medium for Test Line>

A thermal transfer medium for a test line of Comparative Example 9 was obtained in the same manner as in Example 1, except that unlike in the production of the thermal transfer medium for a test line of Example 1, a protective layer coating liquid 27 produced by dissolving fructose (D(−)-fructose available from Wako Pure Chemical Industries, Ltd.) in purified water to be 0.03% by mass was used to form a protective layer having an average thickness of 0.3 μm in a manner to cover the reagent over the surface of the release and solid-phase reagent layer (for immobilization).

<Production of Thermal Transfer Medium for Control Line>

A thermal transfer medium for a control line of Comparative Example 9 was obtained in the same manner as in the production of the thermal transfer medium for a test line of Example 1, except that the protective layer coating liquid 1 used in the production of the thermal transfer medium for a test line of Example 1 was changed to the protective layer coating liquid 27 prepared in the production of the thermal transfer medium for a test line of Comparative Example 9.

Comparative Example 10

An immunochromatoassay (testing device 10) of Comparative Example 10 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-2.

<Production of Thermal Transfer Medium for Test Line>

A thermal transfer medium for a test line of Comparative Example 10 was obtained in the same manner as in Example 1, except that unlike in the production of the thermal transfer medium for a test line of Example 1, a protective layer coating liquid 28 produced by dissolving galactose (D(+)-galactose available from Wako Pure Chemical Industries, Ltd.) in purified water to be 3.5% by mass was used to form a protective layer having an average thickness of 35 μm in a manner to cover the reagent over the surface of the release and solid-phase reagent layer (for immobilization).

<Production of Thermal Transfer Medium for Control Line>

A thermal transfer medium for a control line of Comparative Example 10 was obtained in the same manner as in the production of the thermal transfer medium for a test line of Example 1, except that the protective layer coating liquid 1 used in the production of the thermal transfer medium for a test line of Example 1 was changed to the protective layer coating liquid 28 prepared in the production of the thermal transfer medium for a test line of Comparative Example 10.

Comparative Example 11

An immunochromatoassay (testing device 10) of Comparative Example 11 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-2.

<Production of Thermal Transfer Medium for Test Line>

A thermal transfer medium for a test line of Comparative Example 11 was obtained in the same manner as in Example 1, except that unlike in the production of the thermal transfer medium for a test line of Example 1, a protective layer coating liquid 29 produced by dissolving galactose (D(+)-galactose available from Wako Pure Chemical Industries, Ltd.) in purified water to be 0.03% by mass was used to form a protective layer having an average thickness of 0.3 μm in a manner to cover the reagent over the surface of the release and solid-phase reagent layer (for immobilization).

<Production of Thermal Transfer Medium for Control Line>

A thermal transfer medium for a control line of Comparative Example 11 was obtained in the same manner as in the production of the thermal transfer medium for a test line of Example 1, except that the protective layer coating liquid 1 used in the production of the thermal transfer medium for a test line of Example 1 was changed to the protective layer coating liquid 29 prepared in the production of the thermal transfer medium for a test line of Comparative Example 11.

Comparative Example 12

An immunochromatoassay (testing device 10) of Comparative Example 12 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-2.

<Production of Thermal Transfer Medium for Test Line>

A thermal transfer medium for a test line of Comparative Example 12 was obtained in the same manner as in Example 1, except that unlike in the production of the thermal transfer medium for a test line of Example 1, a protective layer coating liquid 30 produced by dissolving sucrose (available from Wako Pure Chemical Industries, Ltd.) in purified water to be 3.5% by mass was used to form a protective layer having an average thickness of 35 μm in a manner to cover the reagent over the surface of the release and solid-phase reagent layer (for immobilization).

<Production of Thermal Transfer Medium for Control Line>

A thermal transfer medium for a control line of Comparative Example 12 was obtained in the same manner as in the production of the thermal transfer medium for a test line of Example 1, except that the protective layer coating liquid 1 used in the production of the thermal transfer medium for a test line of Example 1 was changed to the protective layer coating liquid 30 prepared in the production of the thermal transfer medium for a test line of Comparative Example 12.

Comparative Example 13

An immunochromatoassay (testing device 10) of Comparative Example 13 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-2.

<Production of Thermal Transfer Medium for Test Line>

A thermal transfer medium for a test line of Comparative Example 13 was obtained in the same manner as in Example 1, except that unlike in the production of the thermal transfer medium for a test line of Example 1, a protective layer coating liquid 31 produced by dissolving sucrose (available from Wako Pure Chemical Industries, Ltd.) in purified water to be 0.03% by mass was used to form a protective layer having an average thickness of 0.3 μm in a manner to cover the reagent over the surface of the release and solid-phase reagent layer (for immobilization).

<Production of Thermal Transfer Medium for Control Line>

A thermal transfer medium for a control line of Comparative Example 13 was obtained in the same manner as in the production of the thermal transfer medium for a test line of Example 1, except that the protective layer coating liquid 1 used in the production of the thermal transfer medium for a test line of Example 1 was changed to the protective layer coating liquid 31 prepared in the production of the thermal transfer medium for a test line of Comparative Example 13.

Comparative Example 14

An immunochromatoassay (testing device 10) of Comparative Example 14 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-2.

<Production of Thermal Transfer Medium for Test Line>

A thermal transfer medium for a test line of Comparative Example 14 was obtained in the same manner as in Example 1, except that unlike in the production of the thermal transfer medium for a test line of Example 1, a protective layer coating liquid 32 produced by dissolving lactose (lactose monohydrate available from Wako Pure Chemical Industries, Ltd.) in purified water to be 3.5% by mass was used to form a protective layer having an average thickness of 35 μm in a manner to cover the reagent over the surface of the release and solid-phase reagent layer (for immobilization).

<Production of Thermal Transfer Medium for Control Line>

A thermal transfer medium for a control line of Comparative Example 14 was obtained in the same manner as in the production of the thermal transfer medium for a test line of Example 1, except that the protective layer coating liquid 1 used in the production of the thermal transfer medium for a test line of Example 1 was changed to the protective layer coating liquid 32 prepared in the production of the thermal transfer medium for a test line of Comparative Example 14.

Comparative Example 15

An immunochromatoassay (testing device 10) of Comparative Example 15 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-2.

<Production of Thermal Transfer Medium for Test Line>

A thermal transfer medium for a test line of Comparative Example 15 was obtained in the same manner as in Example 1, except that unlike in the production of the thermal transfer medium for a test line of Example 1, a protective layer coating liquid 33 produced by dissolving lactose (lactose monohydrate available from Wako Pure Chemical Industries, Ltd.) in purified water to be 0.03% by mass was used to form a protective layer having an average thickness of 0.3 μm in a manner to cover the reagent over the surface of the release and solid-phase reagent layer (for immobilization).

<Production of Thermal Transfer Medium for Control Line>

A thermal transfer medium for a control line of Comparative Example 15 was obtained in the same manner as in the production of the thermal transfer medium for a test line of Example 1, except that the protective layer coating liquid 1 used in the production of the thermal transfer medium for a test line of Example 1 was changed to the protective layer coating liquid 33 prepared in the production of the thermal transfer medium for a test line of Comparative Example 15.

Comparative Example 16

An immunochromatoassay (testing device 10) of Comparative Example 16 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-2.

<Production of Thermal Transfer Medium for Test Line>

A thermal transfer medium for a test line of Comparative Example 16 was obtained in the same manner as in Example 1, except that unlike in the production of the thermal transfer medium for a test line of Example 1, a protective layer coating liquid 34 produced by dissolving maltose (D(+)-maltose monohydrate available from Wako Pure Chemical Industries, Ltd.) in purified water to be 3.5% by mass was used to form a protective layer having an average thickness of 35 μm in a manner to cover the reagent over the surface of the release and solid-phase reagent layer (for immobilization).

<Production of Thermal Transfer Medium for Control Line>

A thermal transfer medium for a control line of Comparative Example 16 was obtained in the same manner as in the production of the thermal transfer medium for a test line of Example 1, except that the protective layer coating liquid 1 used in the production of the thermal transfer medium for a test line of Example 1 was changed to the protective layer coating liquid 34 prepared in the production of the thermal transfer medium for a test line of Comparative Example 16.

Comparative Example 17

An immunochromatoassay (testing device 10) of Comparative Example 17 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-2.

<Production of Thermal Transfer Medium for Test Line>

A thermal transfer medium for a test line of Comparative Example 17 was obtained in the same manner as in Example 1, except that unlike in the production of the thermal transfer medium for a test line of Example 1, a protective layer coating liquid 35 produced by dissolving maltose (D(+)-maltose monohydrate available from Wako Pure Chemical Industries, Ltd.) in purified water to be 0.03% by mass was used to form a protective layer having an average thickness of 0.3 μm in a manner to cover the reagent over the surface of the release and solid-phase reagent layer (for immobilization).

<Production of Thermal Transfer Medium for Control Line>

A thermal transfer medium for a control line of Comparative Example 17 was obtained in the same manner as in the production of the thermal transfer medium for a test line of Example 1, except that the protective layer coating liquid 1 used in the production of the thermal transfer medium for a test line of Example 1 was changed to the protective layer coating liquid 35 prepared in the production of the thermal transfer medium for a test line of Comparative Example 17.

Comparative Example 18

An immunochromatoassay (testing device 10) of Comparative Example 18 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-2.

<Production of Thermal Transfer Medium for Test Line>

A thermal transfer medium for a test line of Comparative Example 18 was obtained in the same manner as in Example 1, except that unlike in the production of the thermal transfer medium for a test line of Example 1, a protective layer coating liquid 36 produced by dissolving cellobiose (D(+)-cellobiose available from Nacalai Tesque, Inc.) in purified water to be 3.5% by mass was used to form a protective layer having an average thickness of 35 μm in a manner to cover the reagent over the surface of the release and solid-phase reagent layer (for immobilization).

<Production of Thermal Transfer Medium for Control Line>

A thermal transfer medium for a control line of Comparative Example 18 was obtained in the same manner as in the production of the thermal transfer medium for a test line of Example 1, except that the protective layer coating liquid 1 used in the production of the thermal transfer medium for a test line of Example 1 was changed to the protective layer coating liquid 36 prepared in the production of the thermal transfer medium for a test line of Comparative Example 18.

Comparative Example 19

An immunochromatoassay (testing device 10) of Comparative Example 19 was produced in the same manner as in Example 1, except that unlike in Example 1, a thermal transfer medium for a test line and thermal transfer medium for a control line produced in the manner described below were used. The immunochromatoassay was evaluated in the same manner as in Example 1. The results are presented in Table 3-2.

<Production of Thermal Transfer Medium for Test Line>

A thermal transfer medium for a test line of Comparative Example 19 was obtained in the same manner as in Example 1, except that unlike in the production of the thermal transfer medium for a test line of Example 1, a protective layer coating liquid 37 produced by dissolving cellobiose (D(+)-cellobiose available from Nacalai Tesque, Inc.) in purified water to be 0.03% by mass was used to form a protective layer having an average thickness of 0.3 μm in a manner to cover the reagent over the surface of the release and solid-phase reagent layer (for immobilization).

<Production of Thermal Transfer Medium for Control Line>

A thermal transfer medium for a control line of Comparative Example 19 was obtained in the same manner as in the production of the thermal transfer medium for a test line of Example 1, except that the protective layer coating liquid 1 used in the production of the thermal transfer medium for a test line of Example 1 was changed to the protective layer coating liquid 37 prepared in the production of the thermal transfer medium for a test line of Comparative Example 19.

The details of the immunochromatoassays (testing devices) of Examples 1 to 22 and Comparative Examples 1 to 19 are collectively presented in Table 1-1 to Table 2-2.

TABLE 1-1

| | Labeled antibody | | | | Test line | | Control line | |
|---|---|---|---|---|---|---|---|---|
| | Antibody | Preparation example | Resin | Preparation example | Antibody | Preparation example | Antibody | Preparation example |
| Ex. 1 | Gold-labeled ahIgG | 6 | Polyvinyl butyral BL-1 | 3 | ahIgG | 4 | hIgG | 5 |
| Ex. 2 | Gold-labeled ahIgG | 6 | Polyvinyl butyral BL-1 | 3 | ahIgG | 4 | hIgG | 5 |
| Ex. 3 | Gold-labeled ahIgG | 6 | Polyvinyl butyral BL-1 | 3 | ahIgG | 4 | hIgG | 5 |
| Ex. 4 | Gold-labeled ahIgG | 6 | Polyvinyl butyral BL-1 | 3 | ahIgG | 4 | hIgG | 5 |
| Ex. 5 | Gold-labeled ahIgG | 6 | Polyvinyl butyral BL-1 | 3 | ahIgG | 4 | hIgG | 5 |
| Ex. 6 | Gold-labeled ahIgG | 6 | Polyvinyl butyral BL-1 | 3 | ahIgG | 4 | hIgG | 5 |
| Ex. 7 | Gold-labeled ahIgG | 6 | Polyvinyl butyral BL-1 | 3 | ahIgG | 4 | hIgG | 5 |
| Ex. 8 | Gold-labeled ahIgG | 6 | Polyvinyl butyral BL-1 | 3 | ahIgG | 4 | hIgG | 5 |
| Ex. 9 | Gold-labeled ahIgG | 6 | Polyvinyl butyral BL-1 | 3 | ahIgG | 4 | hIgG | 5 |
| Ex. 10 | Gold-labeled ahIgG | 6 | Polyvinyl butyral BL-1 | 3 | ahIgG | 4 | hIgG | 5 |
| Ex. 11 | Gold-labeled ahIgG | 6 | Polyvinyl butyral BL-1 | 3 | ahIgG | 4 | hIgG | 5 |
| Ex. 12 | Gold-labeled ahIgG | 6 | Polyvinyl butyral BL-1 | 3 | ahIgG | 4 | hIgG | 5 |
| Ex. 13 | Gold-labeled ahIgG | 6 | Polyvinyl butyral BL-1 | 3 | ahIgG | 4 | hIgG | 5 |
| Ex. 14 | Gold-labeled ahIgG | 6 | Polyvinyl butyral BL-1 | 3 | ahIgG | 4 | hIgG | 5 |
| Ex. 15 | Gold-labeled ahIgG | 6 | Polyvinyl butyral BL-1 | 3 | ahIgG | 4 | hIgG | 5 |
| Ex. 16 | Gold-labeled ahIgG | 6 | Polyvinyl butyral BL-1 | 3 | ahIgG | 4 | hIgG | 5 |
| Ex. 17 | Gold-labeled ahIgG | 6 | Polyvinyl butyral BL-1 | 3 | ahIgG | 4 | hIgG | 5 |
| Ex. 18 | Gold-labeled ahIgG | 6 | Polyvinyl butyral BL-1 | 3 | ahIgG | 4 | hIgG | 5 |
| Ex. 19 | Gold-labeled ahIgG | 6 | Polyvinyl butyral BL-1 | 3 | ahIgG | 4 | hIgG | 5 |
| Ex. 20 | Gold-labeled ahCG | 9 | Polyvinyl butyral BL-1 | 3 | ahCG | 7 | amIgG | 8 |
| Ex. 21 | Gold-labeled ahIgG | 6 | Polyvinyl butyral BL-1 | 3 | ahIgG | 4 | hIgG | 5 |
| Ex. 22 | Gold-labeled ahIgG | 6 | Polyvinyl butyral BL-1 | 3 | ahIgG | 4 | hIgG | 5 |

TABLE 1-2

| | Resin of test line and control line | | Protective layer coating liquid | | | | |
|---|---|---|---|---|---|---|---|
| | Resin | Preparation example | No. | Kind of sugar | Content of sugar (% by mass) | Average thickness of protective layer (μm) | Flow path member |
| Ex. 1 | Carnauba wax, etc. | 2 | 1 | Trehalose | 1 | 10 | Nitrocellulose |
| Ex. 2 | Carnauba wax, etc. | 2 | 2 | Trehalose | 0.05 | 0.5 | Nitrocellulose |
| Ex. 3 | Carnauba wax, etc. | 2 | 3 | Trehalose | 3 | 30 | Nitrocellulose |
| Ex. 4 | Carnauba wax, etc. | 2 | 4 | Inositol | 0.05 | 0.5 | Nitrocellulose |
| Ex. 5 | Carnauba wax, etc. | 2 | 5 | Inositol | 3 | 30 | Nitrocellulose |
| Ex. 6 | Carnauba wax, etc. | 2 | 6 | Glucose | 0.05 | 0.5 | Nitrocellulose |
| Ex. 7 | Carnauba wax, etc. | 2 | 7 | Glucose | 3 | 30 | Nitrocellulose |
| Ex. 8 | Carnauba wax, etc. | 2 | 8 | Fructose | 0.05 | 0.5 | Nitrocellulose |

TABLE 1-2-continued

| | Resin of test line and control line | | Protective layer coating liquid | | | | |
|---|---|---|---|---|---|---|---|
| | Resin | Preparation example | No. | Kind of sugar | Content of sugar (% by mass) | Average thickness of protective layer (μm) | Flow path member |
| Ex. 9 | Carnauba wax, etc. | 2 | 9 | Fructose | 3 | 30 | Nitrocellulose |
| Ex. 10 | Carnauba wax, etc. | 2 | 10 | Galactose | 0.05 | 0.5 | Nitrocellulose |
| Ex. 11 | Carnauba wax, etc. | 2 | 11 | Galactose | 3 | 30 | Nitrocellulose |
| Ex. 12 | Carnauba wax, etc. | 2 | 12 | Sucrose | 0.05 | 0.5 | Nitrocellulose |
| Ex. 13 | Carnauba wax, etc. | 2 | 13 | Sucrose | 3 | 30 | Nitrocellulose |
| Ex. 14 | Carnauba wax, etc. | 2 | 14 | Lactose | 0.05 | 0.5 | Nitrocellulose |
| Ex. 15 | Carnauba wax, etc. | 2 | 15 | Lactose | 3 | 30 | Nitrocellulose |
| Ex. 16 | Carnauba wax, etc. | 2 | 16 | Maltose | 0.05 | 0.5 | Nitrocellulose |
| Ex. 17 | Carnauba wax, etc. | 2 | 17 | Maltose | 3 | 30 | Nitrocellulose |
| Ex. 18 | Carnauba wax, etc. | 2 | 18 | Cellobiose | 0.05 | 0.5 | Nitrocellulose |
| Ex. 19 | Carnauba wax, etc. | 2 | 19 | Cellobiose | 3 | 30 | Nitrocellulose |
| Ex. 20 | Carnauba wax, etc. | 2 | 1 | Trehalose | 1 | 10 | Nitrocellulose |
| Ex. 21 | Carnauba wax, etc. | 2 | 1 | Trehalose | 1 | 10 | Hydrophilic PTFE |
| Ex. 22 | Polyethylene wax, etc. | 10 | 1 | Trehalose | 1 | 10 | Nitrocellulose |

TABLE 2-1

| | Labeled antibody | | | | Test line | | Control line | |
|---|---|---|---|---|---|---|---|---|
| | Antibody | Preparation example | Resin | Preparation example | Antibody | Preparation example | Antibody | Preparation example |
| Comp. Ex. 1 | Gold-labeled ahIgG | 6 | Polyvinyl butyral BL-1 | 3 | ahIgG | 4 | hIgG | 5 |
| Comp. Ex. 2 | Gold-labeled ahIgG | 6 | Polyvinyl butyral BL-1 | 3 | ahIgG | 4 | hIgG | 5 |
| Comp. Ex. 3 | Gold-labeled ahIgG | 6 | Polyvinyl butyral BL-1 | 3 | ahIgG | 4 | hIgG | 5 |
| Comp. Ex. 4 | Gold-labeled ahIgG | 6 | Polyvinyl butyral BL-1 | 3 | ahIgG | 4 | hIgG | 5 |
| Comp. Ex. 5 | Gold-labeled ahIgG | 6 | Polyvinyl butyral BL-1 | 3 | ahIgG | 4 | hIgG | 5 |
| Comp. Ex. 6 | Gold-labeled ahIgG | 6 | Polyvinyl butyral BL-1 | 3 | ahIgG | 4 | hIgG | 5 |
| Comp. Ex. 7 | Gold-labeled ahIgG | 6 | Polyvinyl butyral BL-1 | 3 | ahIgG | 4 | hIgG | 5 |
| Comp. Ex. 8 | Gold-labeled ahIgG | 6 | Polyvinyl butyral BL-1 | 3 | ahIgG | 4 | hIgG | 5 |
| Comp. Ex. 9 | Gold-labeled ahIgG | 6 | Polyvinyl butyral BL-1 | 3 | ahIgG | 4 | hIgG | 5 |
| Comp. Ex. 10 | Gold-labeled ahIgG | 6 | Polyvinyl butyral BL-1 | 3 | ahIgG | 4 | hIgG | 5 |
| Comp. Ex. 11 | Gold-labeled ahIgG | 6 | Polyvinyl butyral BL-1 | 3 | ahIgG | 4 | hIgG | 5 |
| Comp. Ex. 12 | Gold-labeled ahIgG | 6 | Polyvinyl butyral BL-1 | 3 | ahIgG | 4 | hIgG | 5 |
| Comp. Ex. 13 | Gold-labeled ahIgG | 6 | Polyvinyl butyral BL-1 | 3 | ahIgG | 4 | hIgG | 5 |
| Comp. Ex. 14 | Gold-labeled ahIgG | 6 | Polyvinyl butyral BL-1 | 3 | ahIgG | 4 | hIgG | 5 |
| Comp. Ex. 15 | Gold-labeled ahIgG | 6 | Polyvinyl butyral BL-1 | 3 | ahIgG | 4 | hIgG | 5 |
| Comp. Ex. 16 | Gold-labeled ahIgG | 6 | Polyvinyl butyral BL-1 | 3 | ahIgG | 4 | hIgG | 5 |
| Comp. Ex. 17 | Gold-labeled ahIgG | 6 | Polyvinyl butyral BL-1 | 3 | ahIgG | 4 | hIgG | 5 |
| Comp. Ex. 18 | Gold-labeled ahIgG | 6 | Polyvinyl butyral BL-1 | 3 | ahIgG | 4 | hIgG | 5 |
| Comp. Ex. 19 | Gold-labeled ahIgG | 6 | Polyvinyl butyral BL-1 | 3 | ahIgG | 4 | hIgG | 5 |

TABLE 2-2

| | Resin of test line and control line | | Protective layer coating liquid | | | | |
|---|---|---|---|---|---|---|---|
| | Resin | Preparation example | No. | Kind of sugar | Content of sugar (% by mass) | Average thickness of protective layer (μm) | Flow path member |
| Comp. Ex. 1 | Carnauba wax, etc. | 2 | — | | Absent | | Nitrocellulose |
| Comp. Ex. 2 | Carnauba wax, etc. | 2 | 20 | Trehalose | 3.5 | 35 | Nitrocellulose |
| Comp. Ex. 3 | Carnauba wax, etc. | 2 | 21 | Trehalose | 0.03 | 0.3 | Nitrocellulose |
| Comp. Ex. 4 | Carnauba wax, etc. | 2 | 22 | Inositol | 3.5 | 35 | Nitrocellulose |
| Comp. Ex. 5 | Carnauba wax, etc. | 2 | 23 | Inositol | 0.03 | 0.3 | Nitrocellulose |
| Comp. Ex. 6 | Carnauba wax, etc. | 2 | 24 | Glucose | 3.5 | 35 | Nitrocellulose |
| Comp. Ex. 7 | Carnauba wax, etc. | 2 | 25 | Glucose | 0.03 | 0.3 | Nitrocellulose |
| Comp. Ex. 8 | Carnauba wax, etc. | 2 | 26 | Fructose | 3.5 | 35 | Nitrocellulose |
| Comp. Ex. 9 | Carnauba wax, etc. | 2 | 27 | Fructose | 0.03 | 0.3 | Nitrocellulose |
| Comp. Ex. 10 | Carnauba wax, etc. | 2 | 28 | Galactose | 3.5 | 35 | Nitrocellulose |
| Comp. Ex. 11 | Carnauba wax, etc. | 2 | 29 | Galactose | 0.03 | 0.3 | Nitrocellulose |
| Comp. Ex. 12 | Carnauba wax, etc. | 2 | 30 | Sucrose | 3.5 | 35 | Nitrocellulose |
| Comp. Ex. 13 | Carnauba wax, etc. | 2 | 31 | Sucrose | 0.03 | 0.3 | Nitrocellulose |
| Comp. Ex. 14 | Carnauba wax, etc. | 2 | 32 | Lactose | 3.5 | 35 | Nitrocellulose |
| Comp. Ex. 15 | Carnauba wax, etc. | 2 | 33 | Lactose | 0.03 | 0.3 | Nitrocellulose |
| Comp. Ex. 16 | Carnauba wax, etc. | 2 | 34 | Maltose | 3.5 | 35 | Nitrocellulose |
| Comp. Ex. 17 | Carnauba wax, etc. | 2 | 35 | Maltose | 0.03 | 0.3 | Nitrocellulose |
| Comp. Ex. 18 | Carnauba wax, etc. | 2 | 36 | Cellobiose | 3.5 | 35 | Nitrocellulose |
| Comp. Ex. 19 | Carnauba wax, etc. | 2 | 37 | Cellobiose | 0.03 | 0.3 | Nitrocellulose |

TABLE 3-1

| | Line visibility | Reading immediately after production | Reading after sliding | Reading 5 days after production | Temporal stability Degree of degradation (%) | Temporal stability Evaluation |
|---|---|---|---|---|---|---|
| Ex. 1 | A | 156 | 166 | 149 | 4.5 | A |
| Ex. 2 | B | 135 | 130 | 130 | 3.7 | A |
| Ex. 3 | B | 130 | 120 | 120 | 7.7 | A |
| Ex. 4 | B | 135 | 123 | 120 | 11.1 | A |
| Ex. 5 | B | 145 | 140 | 143 | 1.4 | A |
| Ex. 6 | B | 128 | 118 | 118 | 7.8 | A |
| Ex. 7 | B | 131 | 132 | 122 | 6.9 | A |
| Ex. 8 | B | 119 | 109 | 107 | 10.1 | A |
| Ex. 9 | B | 107 | 103 | 98 | 8.4 | A |
| Ex. 10 | B | 121 | 113 | 103 | 14.9 | A |
| Ex. 11 | B | 122 | 125 | 100 | 18.0 | A |
| Ex. 12 | B | 134 | 135 | 124 | 7.5 | A |
| Ex. 13 | B | 132 | 130 | 127 | 3.8 | A |
| Ex. 14 | B | 122 | 111 | 100 | 18.0 | A |
| Ex. 15 | B | 126 | 118 | 104 | 17.5 | A |
| Ex. 16 | B | 133 | 123 | 122 | 8.3 | A |
| Ex. 17 | B | 141 | 139 | 118 | 16.3 | A |
| Ex. 18 | B | 108 | 106 | 89 | 17.6 | A |
| Ex. 19 | B | 100 | 104 | 85 | 15.0 | A |
| Ex. 20 | A | 161 | 159 | 148 | 8.1 | A |
| Ex. 21 | A | 153 | 149 | 139 | 9.2 | A |
| Ex. 22 | A | 149 | 155 | 136 | 8.7 | A |

TABLE 3-2

| | Line visibility | Reading immediately after production | Reading after sliding | Reading 5 days after production | Temporal stability Degree of degradation (%) | Temporal stability Evaluation |
|---|---|---|---|---|---|---|
| Comp. Ex. 1 | B | 116 | 71 | 58 | 50.0 | B |
| Comp. Ex. 2 | C | 80 | 80 | 70 | 12.5 | A |
| Comp. Ex. 3 | B | 120 | 85 | 68 | 43.3 | B |
| Comp. Ex. 4 | C | 70 | 70 | 72 | 2.9 | A |
| Comp. Ex. 5 | B | 121 | 65 | 76 | 37.2 | B |
| Comp. Ex. 6 | C | 91 | 87 | 76 | 16.5 | A |
| Comp. Ex. 7 | B | 123 | 118 | 87 | 29.3 | B |
| Comp. Ex. 8 | C | 87 | 75 | 77 | 11.5 | A |
| Comp. Ex. 9 | B | 100 | 87 | 47 | 53.0 | B |
| Comp. Ex. 10 | C | 62 | 59 | 56 | 9.7 | A |
| Comp. Ex. 11 | B | 112 | 108 | 61 | 45.5 | B |
| Comp. Ex. 12 | C | 73 | 73 | 63 | 13.7 | A |
| Comp. Ex. 13 | B | 122 | 118 | 74 | 39.3 | B |
| Comp. Ex. 14 | C | 82 | 76 | 70 | 14.6 | A |
| Comp. Ex. 15 | B | 118 | 115 | 67 | 43.2 | B |
| Comp. Ex. 16 | C | 77 | 69 | 63 | 18.2 | A |
| Comp. Ex. 17 | B | 114 | 110 | 74 | 35.1 | B |
| Comp. Ex. 18 | C | 58 | 49 | 56 | 3.4 | A |
| Comp. Ex. 19 | B | 98 | 80 | 55 | 43.9 | B |

From the results presented in Table 3-1 and Table 3-2, Examples 1 to 22 each having a protective layer with an optimum average thickness were suppressed in degradation of color development on the line due to sliding and temporal degradation of the reagent, and were able to be confirmed to have a uniform color development on the line.

In contrast, Comparative Example 1 without a protective layer underwent degradation due to friction and temporal degradation of the reagent, and had a poor color development on the line.

Comparative Examples 2, 4, 6, 8, 10, 12, 14, 16, and 18 each having a protective layer with an extremely large average thickness of 35 μm had a poor color development on the line. This is considered due to inhibition by the protective layer against reaction between the capture antibody and the analyte.

Comparative Examples 3, 5, 7, 9, 11, 13, 15, 17, and 19 each having a protective layer with a small average thickness of 0.3 μm had a good color development on the line, but underwent degradation due to friction and degradation of color development on the line due to temporal degradation. This is considered due to failure of the extremely thin protective layer to fulfill the protecting function.

Aspects of the present invention are as follows, for example.

<1> A thermal transfer medium for a testing device, the thermal transfer medium including:

a support:

a solid-phase reagent layer provided over the support and containing a reagent over a surface of the solid-phase reagent layer; and a protective layer provided over the solid-phase reagent layer in a manner to cover the reagent, wherein an average thickness of the protective layer is 0.5 μm or greater but 30 μm or less.

<2> The thermal transfer medium for a testing device according to <1>,
wherein the average thickness of the protective layer is 1 μm or greater but 20 μm or less.
<3> The thermal transfer medium for a testing device according to <1> or <2>, further including
a back layer over a surface of the support opposite to a surface over which the solid-phase reagent layer is provided.
<4> The thermal transfer medium for a testing device according to any one of <1> to <3>,
wherein the reagent is an antibody, and
wherein the protective layer contains a sugar.
<5> The thermal transfer medium for a testing device according to <4>,
wherein the antibody is a capture antibody.
<6> The thermal transfer medium for a testing device according to <4> or <5>,
wherein the sugar is either a monosaccharide or an oligosaccharide.
<7> The thermal transfer medium for a testing device according to any one of <4> to <6>,
wherein the sugar is at least one selected from the group consisting of glucose, fructose, galactose, inositol, sucrose, lactose, maltose, trehalose, and cellobiose.
<8> The thermal transfer medium for a testing device according to any one of <4> to <7>,
wherein the sugar is at least any one of trehalose and inositol.
<9> The thermal transfer medium for a testing device according to any one of <4> to <8>,
wherein a content of the sugar in the protective layer is 0.5% by mass or greater but 30% by mass or less.
<10> The thermal transfer medium for a testing device according to any one of <1> to <9>,
wherein the solid-phase reagent layer contains a thermoplastic resin containing a hydrophobic group.
<11> The thermal transfer medium for a testing device according to <10>,
wherein the resin containing a hydrophobic group is at least one selected from the group consisting of polystyrene-based resins such as polystyrenes and acrylonitrile-butadiene-styrene copolymers, polypropylene resins, polyethylene resins, ethylene-propylene copolymers, polyolefin-based resins, cyclic polyolefin-based resins, polycarbonate resins, polyethylene terephthalate resins, polymethyl methacrylate resins, methacrylic resins, vinyl chloride resins, polybutylene terephthalate resins, polyarylate resins, polysulfone resins, polyether sulfone resins, polyether ether ketone resins, polyether imide resins, fluororesins, polymethylpentene resins, acrylic-based resins such as polyacrylonitrile, and propionate resins.
<12> The thermal transfer medium for a testing device according to any one of <1> to <11>, further including a release layer between the support and the solid-phase reagent layer.
<13> The thermal transfer medium for a testing device according to any one of <1> to <11>,
wherein the solid-phase reagent layer is a release and solid-phase reagent layer serving also as a release layer.
<14> The thermal transfer medium for a testing device according to any one of <1> to <13>,
wherein the thermal transfer medium is a wound body having a roll form.
<15> A method for producing a testing device, the method including a step of bringing the protective layer and the solid-phase reagent layer of the thermal transfer medium for a testing device according to any one of <1> to <14> into contact with a porous flow path member to transfer the protective layer and the solid-phase reagent layer onto the flow path member.
<16> A testing device including:
a porous flow path member including a flow path through which an analyte is flowed; and
a resin layer provided at at least one position on the flow path member, wherein a solid-phase reagent provided over a surface of the resin layer facing the flow path member contains an antibody, and
wherein the solid-phase reagent is covered with a protective layer containing a sugar.
<17> The testing device according to <16>,
wherein the flow path member has a voidage of 40% or higher but 90% or lower.
<18> The testing device according to <16> or <17>,
wherein an average thickness of the flow path member is 0.01 mm or greater but 0.3 mm or less.
<19> A testing kit including:
the testing device according to any one of <16> to <18>; and
at least one selected from the group consisting of an analyte collecting unit configured to collect an analyte and a liquid for treating the analyte.
<20> A testing method including:
a step of supplying an analyte to the flow path member of the testing device according to any one of <16> to <18>; and
a step of bringing the reagent formed as a solid phase over the resin layer into contact with the analyte to release the reagent from the resin layer.
<21> A testing method including
a step of supplying an analyte to the flow path member of the testing device according to any one of <16> to <18>; and
a step of making the reagent formed as a solid phase over the resin layer capture a part of the analyte.

The thermal transfer medium for a testing device according to any one of <1> to <14>, the method for producing a testing device according to <15>, the testing device according to any one of <16> to <18>, the testing kit according to <19>, and the testing method according to <20> or <21> can solve the various problems in the related art and achieve the object of the present invention.

What is claimed is:

1. A thermal transfer medium for a testing device, the thermal transfer medium comprising:
a support;
a solid-phase reagent layer that is provided over the support and comprises a reagent over a surface of the solid-phase reagent layer; and
a protective layer provided over the solid-phase reagent layer in a manner to cover the reagent,
wherein an average thickness of the protective layer is from 0.5 μm to 30 μm,
wherein the reagent comprises an antibody, and
wherein the protective layer comprises a sugar.

2. The thermal transfer medium according to claim 1, further comprising a back layer over a surface of the support opposite to a surface over which the solid-phase reagent layer is provided.

3. The thermal transfer medium according to claim 1, wherein the sugar comprises either a monosaccharide or an oligosaccharide.

4. The thermal transfer medium according to claim 1, wherein the sugar comprises at least one selected from the group consisting of glucose, fructose, galactose, inositol, sucrose, lactose, maltose, trehalose, and cellobiose.

5. The thermal transfer medium according to claim 1, wherein the solid-phase reagent layer comprises a thermoplastic resin that comprises a hydrophobic group.

6. The thermal transfer medium to claim 1, further comprising a release layer between the support and the solid-phase reagent layer.

7. The thermal transfer medium according to claim 1, wherein the solid-phase reagent layer is a release layer.

8. A method for producing a testing device, the method comprising:

bringing a protective layer and a solid-phase reagent layer of a thermal transfer medium for a testing device into contact with a porous flow path member to transfer the protective layer and the solid-phase reagent layer onto the flow path member, wherein the thermal transfer medium comprises:

a support;

the solid-phase reagent layer that is provided over the support and comprises a reagent over a surface of the solid-phase reagent layer; and the protective layer provided over the solid-phase reagent layer in a manner to cover the reagent, wherein an average thickness of the protective layer is from 0.5 μm to 30 μm, wherein the reagent comprises an antibody, and wherein the protective layer comprises a sugar.

9. A testing device comprising:

a porous flow path member that comprises a flow path through which an analyte is flowed; and a resin layer provided at at least one position on the flow path member, wherein a solid-phase reagent provided over a surface of the resin layer facing the flow path member comprises an antibody, and wherein the solid-phase reagent is covered with a protective layer that comprises a sugar.

10. A testing kit comprising:

the testing device according to claim 9; and at least one selected from the group consisting of an analyte collecting unit configured to collect an analyte and a liquid for treating the analyte.

* * * * *